US012186392B2

(12) United States Patent
Klein et al.

(10) Patent No.: US 12,186,392 B2
(45) Date of Patent: Jan. 7, 2025

(54) COMBINATION THERAPY OF AN ANTI CD20 ANTIBODY WITH A BTK INHIBITOR

(71) Applicants: Ono Pharmaceutical Co., Ltd., Osaka (JP); HOFFMANN-LA ROCHE INC., Little Falls, NJ (US)

(72) Inventors: Christian Klein, Bonstetten (CH); Toshio Yoshizawa, Osaka (JP); Tomoko Yasuhiro, Osaka (JP)

(73) Assignees: Ono Pharmaceutical Co., Ltd., Osaka (JP); Hoffmann-La Roche Inc., Little Falls, NJ (US)

( * ) Notice: Subject to any disclaimer, the term of this patent is extended or adjusted under 35 U.S.C. 154(b) by 442 days.

(21) Appl. No.: 16/679,483

(22) Filed: Nov. 11, 2019

(65) Prior Publication Data

US 2020/0171153 A1    Jun. 4, 2020

Related U.S. Application Data

(63) Continuation of application No. 14/532,247, filed on Nov. 4, 2014, now abandoned.

(30) Foreign Application Priority Data

Nov. 7, 2013  (EP) .................................. 13192006

(51) Int. Cl.
| | |
|---|---|
| A61K 39/395 | (2006.01) |
| A61K 31/522 | (2006.01) |
| A61K 39/40 | (2006.01) |
| A61K 45/06 | (2006.01) |
| C07K 16/28 | (2006.01) |
| A61K 39/00 | (2006.01) |
| C07K 16/00 | (2006.01) |

(52) U.S. Cl.
CPC ...... *A61K 39/39558* (2013.01); *A61K 31/522* (2013.01); *A61K 45/06* (2013.01); *C07K 16/2887* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 7,312,243 B1 | 12/2007 | Pravda | |
| 8,008,449 B2 | 8/2011 | Korman et al. | |
| 9,199,997 B2 * | 12/2015 | Yamamoto | .............. A61P 35/02 |
| 2013/0079327 A1 * | 3/2013 | Yamamoto | .............. A61P 43/00 |
| | | | 514/263.22 |
| 2015/0210769 A1 | 7/2015 | Freeman et al. | |

FOREIGN PATENT DOCUMENTS

| | | | | |
|---|---|---|---|---|
| WO | WO-2011152351 A1 * | 12/2011 | ........... | A61K 31/522 |
| WO | WO-2013059738 A2 * | 4/2013 | ........... | A61K 31/337 |
| WO | WO-2013081016 A1 * | 6/2013 | ........... | A61K 31/522 |
| WO | 2014194254 A1 | 12/2014 | | |
| WO | 2015083008 A1 | 6/2015 | | |
| WO | 2016024228 A1 | 2/2016 | | |

OTHER PUBLICATIONS

Hauptrock et al. Biologics: Targets & Therapy 2008, 2(4):619-633. (Year: 2008).*
The US Office Action, mailed Feb. 13, 2020, in relevant U.S. Appl. No. 15/764,547.
The English translation of the Taiwanese Office Action, mailed on Apr. 23, 2020, in relevant Taiwanese Patent Appl. No. 105119835.
Bryan et al., "Role of rituximab in first-line treatment of chronic lymphocytic leukemia," Ther. Clin. Risk Manag., (2011), 7:1-11.
Ricci et al., "Fludarabine in the treatment of chronic lymphocytic leukemia: a review," Ther. Clin. Risk Manag., (2009), 5:187-207.
Parikh et al., "How we treat Richter syndrome," Blood, (2014), 123[11]:1647-1657.
CLL Trialists' Collaborative Group, "Chemotherapeutic Options in Chronic Lymphocytic Leukemia: a Meta-analysis of the Randomized Trials," J. Natl. Cancer Inst., (1999), 91[10]:861-868.
Appendix A: Tirabrutinib (ONO-4059) I Btk Inhibitor I MedChemExpress, Feb. 10, 2020.
Appendix B: Typical Treatment of Chronic Lymphocytic Leukemia, Feb. 12, 2020.
Salles et al. "Obinutuzumab (GA101) in Patients With Relapsed/Refractory Indolent Non-Hodgkin Lymphoma: Results From the Phase II GAUGUIN Study". Journal of Clinical OncologyStudy, vol. 31 (23) p. 2920-2927, Aug. 10, 2013.

* cited by examiner

*Primary Examiner* — Chun W Dahle

(57) ABSTRACT

The present invention is directed to the combination therapy of an anti-CD20 antibody with a BTK inhibitor for the treatment of cancer, especially to the combination therapy of CD20 expressing cancers with a type I anti-CD20 antibody or an afucosylated humanized B-Ly1 antibody and a BTK inhibitor.

4 Claims, 5 Drawing Sheets

Specification includes a Sequence Listing.

COMBINATION THERAPY OF AN ANTI CD20 ANTIBODY WITH A BTK INHIBITOR

CROSS-REFERENCE TO RELATED APPLICATIONS

This application is a Continuation of U.S. patent application Ser. No. 14/532,247, filed Nov. 4, 2014, which claims priority from European Patent Application No. 13192006.8, filed on Nov. 7, 2013, which are all hereby incorporated by reference in all of their entireties.

REFERENCE TO AN ELECTRONIC SEQUENCE LISTING

The instant application contains a Sequence Listing which has been submitted electronically in ASCII format and is herein incorporated by reference in its entirety. Said ASCII copy, created on Feb. 19, 2020, is named SequenceListing.txt and is 23.8 KB in size.

TECHNICAL FIELD

The present invention is directed to the combination therapy of an anti CD20 antibody with a BTK inhibitor for the treatment of cancer.

BACKGROUND OF THE INVENTION

Afucosylated Antibodies

Cell-mediated effector functions of monoclonal antibodies can be enhanced by engineering their oligosaccharide component as described in Umaña, P., et al., Nature Biotechnol. 17 (1999) 176-180; and U.S. Pat. No. 6,602,684. IgG1 type antibodies, the most commonly used antibodies in cancer immunotherapy, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol. Rev. 163 (1998) 59-76; Wright, A., and Morrison, S. L., Trends Biotechnol. 15 (1997) 26-32). Umaña, P., et al., Nature Biotechnol. 17 (1999) 176-180 and WO 99/154342 showed that overexpression in Chinese hamster ovary (CHO) cells of ß(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the N297 carbohydrate or its elimination affect also binding to Fc binding to FcγR and C1 q (Umaña, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R. L., et al., J. Biol. Chem. 276 (2001) 6591-6604; Shields, R. L., et al., J. Biol. Chem. 277 (2002) 26733-26740; Simmons, L. C., et al., J. Immunol. Methods 263 (2002) 133-147).

Studies discussing the activities of afucosylated and fucosylated antibodies, including anti-CD20 antibodies, have been reported (e.g., Iida, S., et al., Clin. Cancer Res. 12 (2006) 2879-2887; Natsume, A., et al., J. Immunol. Methods 306 (2005) 93-103; Satoh, M., et al., Expert Opin. Biol. Ther. 6 (2006) 1161-1173; Kanda, Y., et al., Biotechnol. Bioeng. 94 (2006) 680-688; Davies, J., et al., Biotechnol. Bioeng. 74 (2001) 288-294.

CD20 and Anti CD20 Antibodies

The CD20 molecule (also called human B-lymphocyte-restricted differentiation antigen or Bp35) is a hydrophobic transmembrane protein located on pre-B and mature B lymphocytes that has been described extensively (Valentine, M. A., et al., J. Biol. Chem. 264 (1989) 11282-11287; and Einfeld, D. A., et al., EMBO J. 7 (1988) 711-717; Tedder, T. F., et al., Proc. Natl. Acad. Sci. U.S.A. 85 (1988) 208-212; Stamenkovic, I., et al., J. Exp. Med. 167 (1988) 1975-1980; Tedder, T. F., et al., J. Immunol. 142 (1989) 2560-2568). CD20 is expressed on greater than 90% of B cell non-Hodgkin's lymphomas (NHL) (Anderson, K. C., et al., Blood 63 (1984) 1424-1433) but is not found on hematopoietic stem cells, pro-B cells, normal plasma cells, or other normal tissues (Tedder, T. F., et al., J, Immunol. 135 (1985) 973-979).

There exist two different types of anti-CD20 antibodies differing significantly in their mode of CD20 binding and biological activities (Cragg, M. S., et al., Blood 103 (2004) 2738-2743; and Cragg, M. S., et al., Blood 101 (2003) 1045-1052).

Type I antibodies, as, e.g., rituximab (a non-afucosylated antibody with an amount of fucose of 85% or higher), ofatumumab, veltuzumab, ocrelizumab are potent in complement mediated cytotoxicity.

Type II antibodies, as e.g. Tositumomab (B1), 11B8, AT80 or humanized B-Ly1 antibodies, effectively initiate target cell death via caspase-independent cell death induction with concomitant phosphatidylserine exposure.

BTK and BTK Inhibitors

Bruton's tyrosine kinase or Bruton agammaglobulinemia tyrosine kinase (abbreviated Btk or BTK) is a member of the TEC family of kinases. BTK is associated with the primary immunodeficiency disease X-linked agammaglobulinemia (Bruton's agammaglobulinemia). The exact mechanism of action is unknown. The BTK gene encodes the BTK protein, which is crucial for the development and maturation of B cells as mast cell activation through the high-affinity IgE receptor. Patients with X-linked agammaglobulinemia have normal pre-B cell populations in the bone marrow, however, these cells fail to mature and enter the circulation. The BTK gene is located on the X chromosome. More than 400 mutations of the BTK gene have been identified.

BTK is activated upstream by Src-family kinases Blk, Lyn and Fyn and leads to downstream activation of essential cell survival pathways such as NF-κB and MAP kinase. BTK contains a pleckstrin-homology (PH) domain that binds phosphatidylinositol (3,4,5)-trisphosphate (PI(3,4,5)$P_3$). PI(3,4,5)$P_3$ binding induces Btk to phosphorylate phospholipase Cγ (PLCγ), which in turn hydrolyzes PI(4,5)P2, a phosphatidylinositol, into two second messengers, inositol triphosphate (IP3) and diacylglycerol (DAG), which then go on to modulate the activity of downstream proteins during B-cell signalling. Subsequently, $Ca^{2+}$ is mobilized and NF-κB and MAP kinase pathways are activated.

An exemplary BTK inhibitor described in the art is ibrutinib (PCI-32765; Advani et al.; J Clin Oncol. 2013: Jan. 1; 31(1), page 88-94) which is a small molecule irreversible BTK inhibitor.

SUMMARY OF THE INVENTION

We have now found out that the combination of type I anti-CD20 antibody, or an afucosylated, type II anti-CD20 antibody with a BTK inhibitor showed significantly enhanced antiproliferative effects. Surprisingly, this combination is more than additive, i.e. highly synergistic.

One aspect of the invention is an afucosylated anti-CD20 antibody with an amount of fucose of 60% or less of the total amount of oligosaccharides (sugars) at Asn297, for the treatment of cancer in combination with a BTK inhibitor.

Another aspect of the invention is the use of an afucosylated anti-CD20 antibody with an amount of fucose of 60% or less of the total amount of oligosaccharides (sugars) at Asn297, for the manufacture of a medicament for the treatment of cancer in combination with a BTK inhibitor.

Another aspect of the invention is a method of treatment of patient suffering from cancer by administering an afucosylated anti-CD20 antibody with an amount of fucose of 60% or less of the total amount of oligosaccharides (sugars) at Asn297, in combination with a BTK inhibitor, to a patient in the need of such treatment.

In one embodiment, the amount of fucose is between 40% and 60% of the total amount of oligosaccharides (sugars) at Asn297. In another embodiment, the amount of fucose is 0% of the total amount of oligosaccharides (sugars) at Asn297.

In one embodiment, the type I anti-CD20 antibody is rituximab. In one embodiment, the afucosylated anti-CD20 antibody is an IgG1 antibody. In another embodiment, said cancer is a CD20 expressing cancer, preferably a lymphoma or lymphocytic leukemia. In one embodiment said afucosylated anti-CD20 antibody is humanized B-Ly1 antibody. In another embodiment, said afucosylated antibody is a type II anti-CD20 antibody.

In one embodiment, said BTK inhibitor is a compound selected from the compounds described in WO2011/152351 and WO2013/081016. Said BTK inhibitor preferably is a compound according to formula I or according to formula I-1 as disclosed herein. Preferably, the BTK inhibitor is 6-amino-9-[(3R)-1-(2-butynoyl)-3-pyrrolidinyl]-7-(4-phenoxyphenyl)-7,9-dihydro-8H-purin-8-one or a salt thereof.

In one embodiment, said type I anti-CD20 antibody is rituximab, said afucosylated anti-CD20 antibody is humanized B-Ly1 antibody and said BTK inhibitor is selected from the group consisting of: the compounds described in WO2011/152351 and WO2013/081016. Said BTK inhibitor preferably is a compound according to formula I or according to formula I-1 as disclosed herein. Preferably, the BTK inhibitor is 6-amino-9-[(3R)-1-(2-butynoyl)-3-pyrrolidinyl]-7-(4-phenoxyphenyl)-7,9-dihydro-8H-purin-8-one or a salt thereof, and said cancer is a CD20 expressing cancer, in one embodiment a lymphoma or lymphocytic leukemia.

In one embodiment, the afucosylated anti-CD20 antibody binds CD20 with an KD of $10^{-8}$ M to $10^{-13}$ M.

One embodiment of the invention is a pharmaceutical composition comprising a combination of a type I anti-CD20 antibody (in one embodiment rituximab) or an afucosylated anti-CD20 antibody with an amount of fucose of 60% or less of the total amount of oligosaccharides (sugars) at Asn297, (in one embodiment an afucosylated humanized B-Ly1 antibody), and a BTK inhibitor (in one embodiment, the BTK inhibitor is selected from the group consisting of: the compounds described in WO2011/152351 and WO2013/081016. Said BTK inhibitor preferably is a compound according to formula I or according to formula I-1 as disclosed herein. Preferably, the BTK inhibitor is 6-amino-9-[(3R)-1-(2-butynoyl)-3-pyrrolidinyl]-7-(4-phenoxyphenyl)-7,9-dihydro-8H-purin-8-one or a salt thereof) for the treatment of cancer.

Figure 1A:
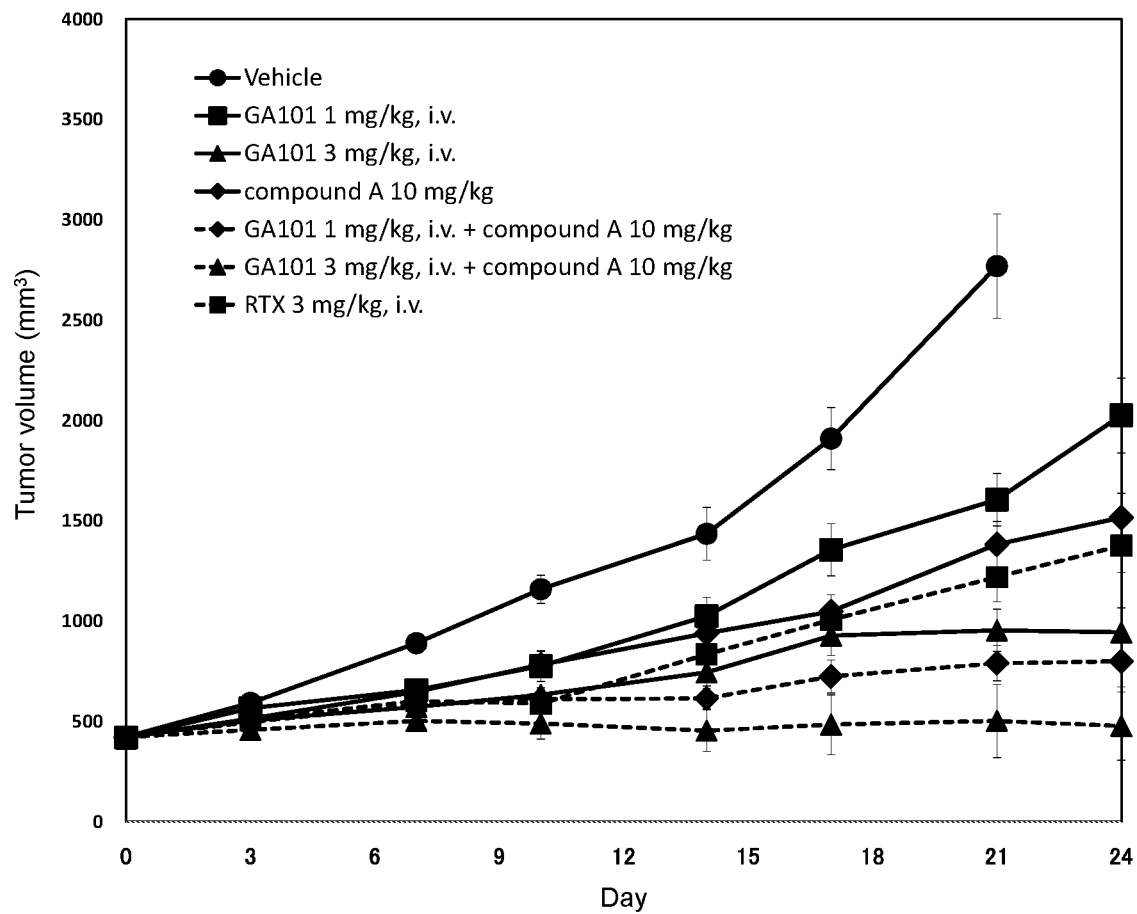
FIGS. 1A-1B: Antitumour activity study: Mean tumour volume curves 1A and Median tumour volume curves 1B of mice bearing subcutaneous TMD8 cells.
Figure 1B:
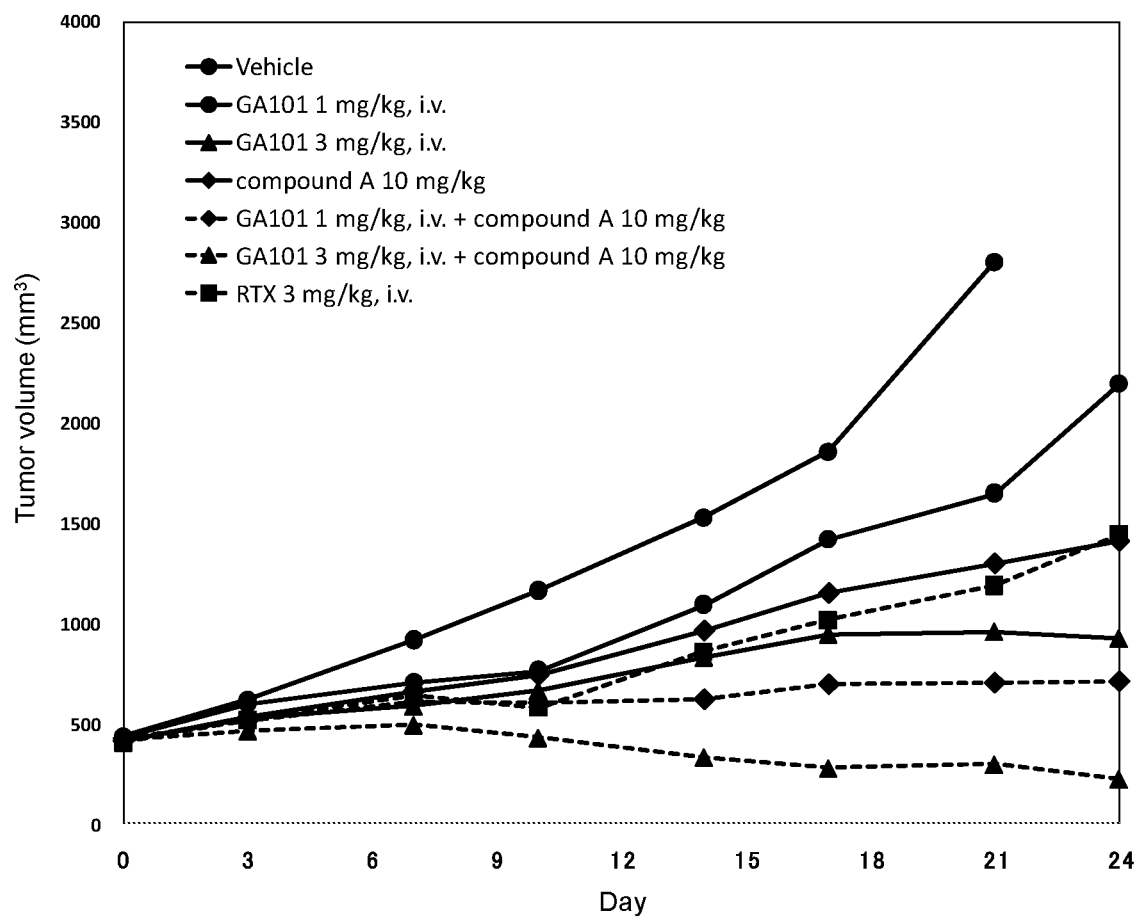

Mice were xenografted on DO. Randomization was performed on D14 (Day 0 as indicated in FIGS. 1A-1B). Mice received one PO administration of vehicle and compound A at 10 mg/kg twice every day (Q0.5D×24) alone or in combination with one IV injection of GA101 at 1 and 3 mg/kg once a week (Q7D×4). Mice received one IV injection of Rituximab (at 3 mg/kg) or one IV injection of GA101 (at 1 and 3 mg/kg) once a week (D14 (Day 0), 21 (Day 7), 28 (Day 14) and D35 (Day 21): Q7D×4). Tumor volumes were monitored and recorded twice a week.

Figure 2A:
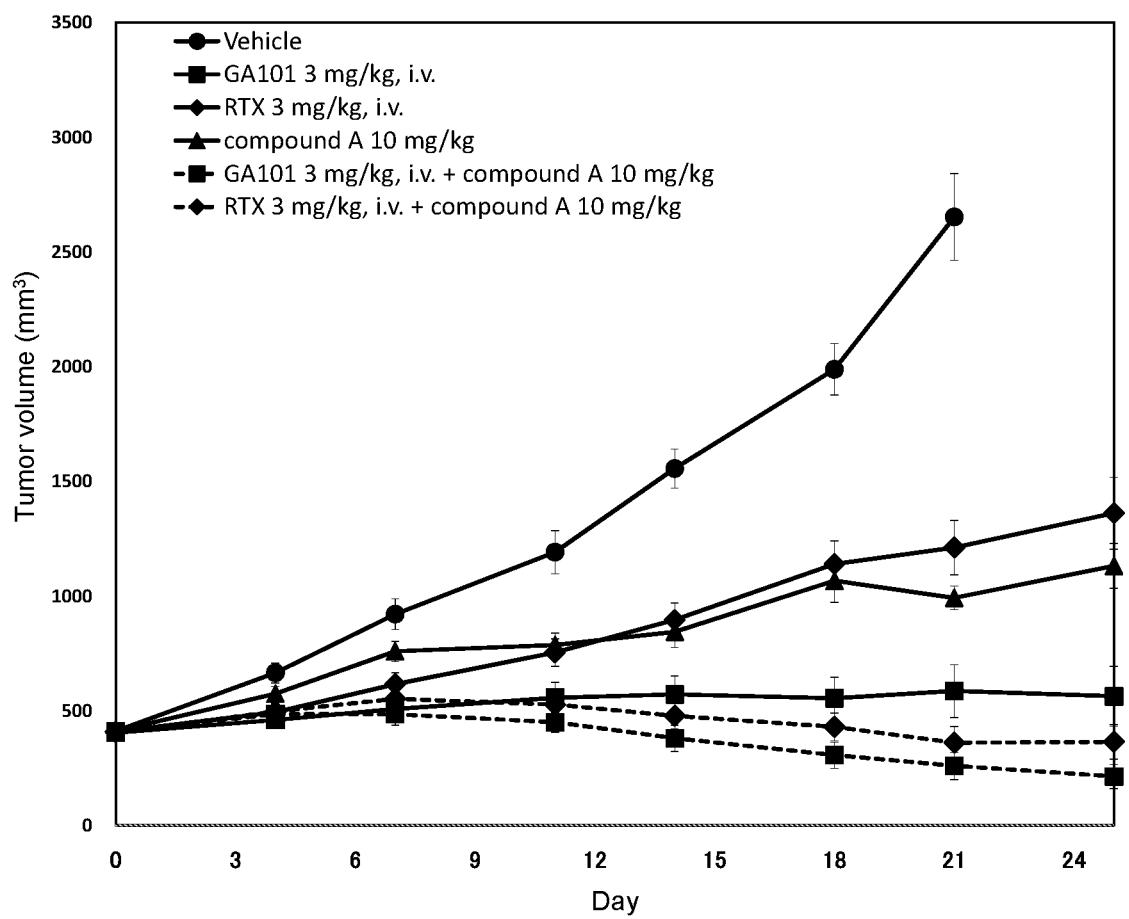
Figure 2B:
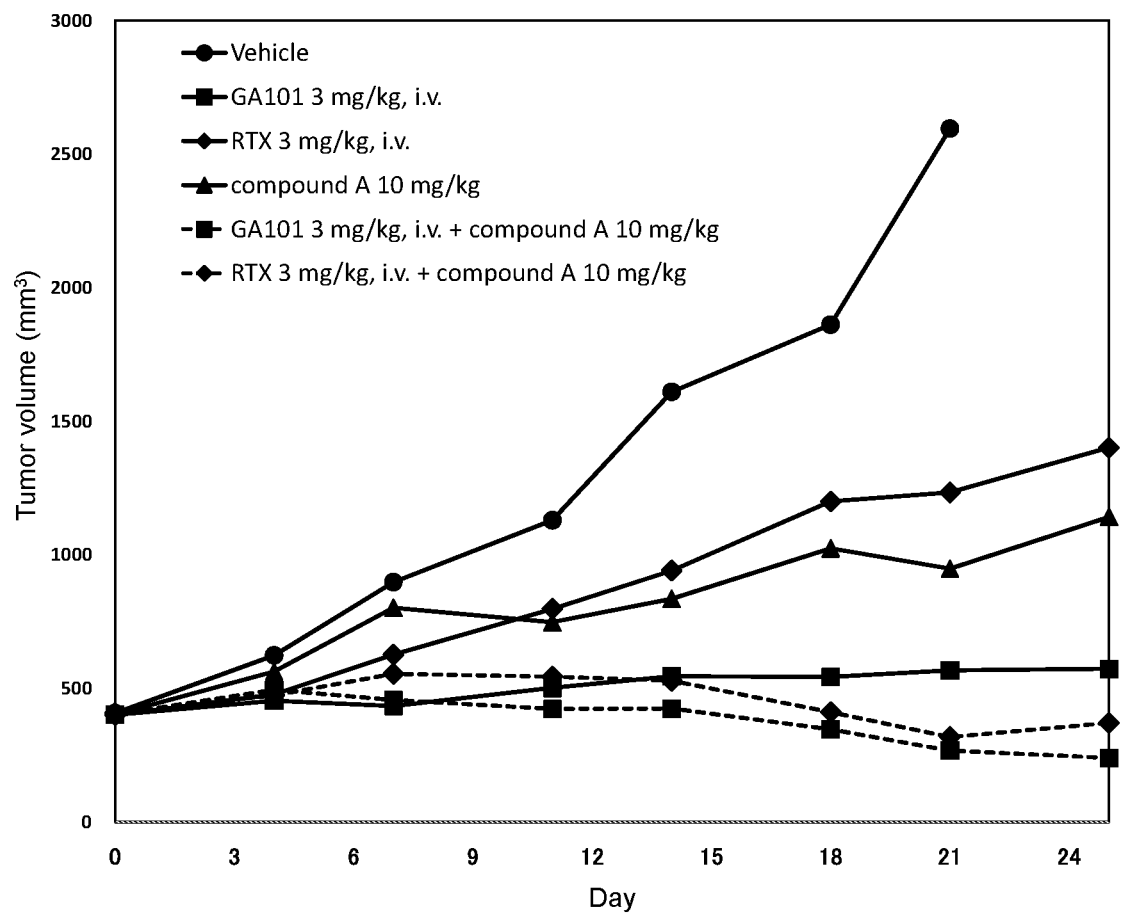

FIGS. 2A-2B: Antitumor activity study: Mean tumour volume curves 1A and Median tumour volume curves 1B of mice bearing subcutaneous TMD8 cells.

Mice were xenografted on DO. Randomization was performed on D14(400-450 mm$^3$: Day 0 as indicated in FIGS. 2A-2B). Mice received one PO administration of vehicle and compound A at 10 mg/kg twice every day (Q0.5D×24) alone or in combination with one IV injection of GA101/RTX at 3 mg/kg once a week (Q7D×4). Mice received one IV injection of Rituximab (at 3 mg/kg) or one IV injection of GA101 (at 3 mg/kg) once a week (D14 (Day 0), 21 (Day 7), 28 (Day 14) and 35 (Day 21): Q7D×4). Tumor volumes were monitored and recorded twice a week.

Figure 3:
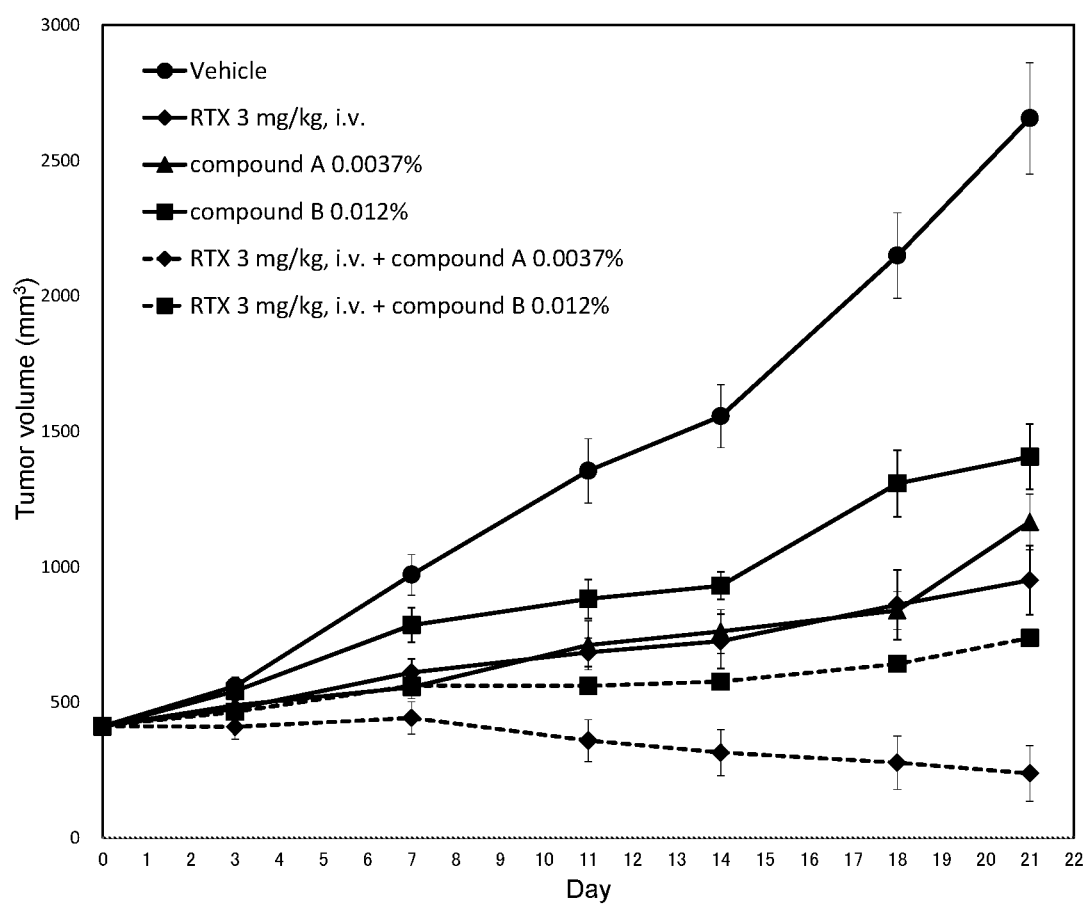

FIG. 3: Antitumor activity study: Mean tumour volume curves of mice bearing subcutaneous TMD8 cells.

Mice were xenografted on DO. Randomization was performed on D14 (around 450 mm$^3$: Day 0 as indicated in FIG. 3). Mice fed a diet containing compound A at 0.0037% (converted to 6 mg/kg/day) or compound B at 0.012% (converted to 20 mg/kg/day) alone, or in combination with one IV injection of RTX at 3 mg/kg once a week (Q7D×3). Mice received one IV injection of Rituximab (at 3 mg/kg) once a week (D14 (Day 0), 21 (Day 7) and 28 (Day 14): Q7D×3). Tumor volumes were monitored and recorded at Day 3, Day 7, Day 11, Day 14, Day 18 and Day 21.

DETAILED DESCRIPTION OF THE INVENTION

The invention comprises a type I anti-CD20 antibody, or an afucosylated anti-CD20 antibody of IgG1 or IgG3 isotype with an amount of fucose of 60% or less of the total amount of oligosaccharides (sugars) at Asn297, for the treatment of cancer in combination with a BTK inhibitor.

The invention comprises the use of a type I anti-CD20 antibody, or an afucosylated anti-CD20 antibody of IgG1 or IgG3 isotype with an amount of fucose of 60% or less of the total amount of oligosaccharides (sugars) at Asn297, for the manufacture of a medicament for the treatment of cancer in combination with a BTK inhibitor.

In one embodiment, the amount of fucose is between 40% and 60% of the total amount of oligosaccharides (sugars) at Asn297.

The term "antibody" encompasses the various forms of antibodies including but not being limited to whole antibodies, human antibodies, humanized antibodies and genetically engineered antibodies like monoclonal antibodies, chimeric antibodies or recombinant antibodies as well as fragments of such antibodies as long as the characteristic properties according to the invention are retained. The terms "monoclonal antibody" or "monoclonal antibody composition" as used herein refer to a preparation of antibody molecules of a single amino acid composition. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g. a transgenic mouse, having a genome comprising a human heavy chain transgene and a light human chain transgene fused to an immortalized cell.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L. et al., Nature 332 (1988) 323-327; and Neuberger, M. S. et al., Nature 314 (1985) 268-270. Particularly preferred CDRs correspond to those representing sequences recognizing the antigens noted above for chimeric and bi- or multispecific antibodies.

The term "human antibody", as used herein, is intended to include antibodies having variable and constant regions derived from human germline immunoglobulin sequences. Human antibodies are well-known in the state of the art (van Dijk, M. A., and van de Winkel, J. G., Curr. Opin. in Chem. Biol. 5 (2001) 368-374). Based on such technology, human antibodies against a great variety of targets can be produced. Examples of human antibodies are for example described in Kellermann, S. A., et al., Curr Opin Biotechnol. 13 (2002) 593-597.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form. The recombinant human antibodies according to the invention have been subjected to in vivo somatic hypermutation. Thus, the amino acid sequences of the VH and VL regions of the recombinant antibodies are sequences that, while derived from and related to human germline VH and VL sequences, may not naturally exist within the human antibody germline repertoire in vivo.

The term "bi- or multispecific antibody" as used herein relates to monoclonal antibodies that have binding specificities for at least two different sites. In certain embodiments, one of the binding specificities is for CD20 and the other is for any other antigen. In certain embodiments, bispecific antibodies may bind to two different epitopes of CD20. Bispecific antibodies may also be used to localize cytotoxic agents to cells which express CD20. Bispecific antibodies can be prepared as full length antibodies or antibody fragments.

As used herein, the term "binding" or "specifically binding" refers to the binding of the antibody to an epitope of the tumor antigen in an in vitro assay, preferably in an plasmon resonance assay (BIAcore, GE-Healthcare Uppsala, Sweden) with purified wild-type antigen. The affinity of the binding is defined by the terms ka (rate constant for the association of the antibody from the antibody/antigen complex), $k_D$ (dissociation constant), and $K_D$ ($k_D$/ka). Binding or specifically binding means a binding affinity ($K_D$) of $10^{-8}$ M or less, preferably $10^{-8}$ M to $10^{-13}$ M (in one embodiment $10^{-9}$ M to $10^{-13}$ M). Thus, an afucosylated antibody according to the invention is specifically binding to the tumor antigen with a binding affinity ($K_D$) of $10^{-8}$ mol/l or less, preferably $10^{-8}$ M to $10^{-13}$ M (in one embodiment $10^{-9}$ M to $10^{-13}$ M).

The term "nucleic acid molecule", as used herein, is intended to include DNA molecules and RNA molecules. A nucleic acid molecule may be single-stranded or double-stranded, but preferably is double-stranded DNA.

The "constant domains" are not involved directly in binding the antibody to an antigen but are involved in the effector functions (ADCC, complement binding, and CDC).

The "variable region" (variable region of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a B-sheet conformation and the CDRs may form loops connecting the B-sheet structure. The CDRs in each chain are held in their three-dimensional structure by the framework regions and form together with the CDRs from the other chain the antigen binding site.

The terms "hypervariable region" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. Especially, CDR3 of the heavy chain is the region which contributes most to antigen binding. CDR and FR regions are determined according to the standard definition of Kabat, et al., Sequences of Proteins of Immunological Interest, 5th ed., Public Health Service, National Institutes of Health, Bethesda, MD (1991), and/or those residues from a "hypervariable loop".

The term "afucosylated antibody" refers to an antibody of IgG1 or IgG3 isotype (preferably of IgG1 isotype) with an altered pattern of glycosylation in the Fc region at Asn297 having a reduced level of fucose residues. Glycosylation of human IgG1 or IgG3 occurs at Asn297 as core fucosylated bianntennary complex oligosaccharide glycosylation terminated with up to 2 Gal residues. These structures are designated as G0, G1 (α1,6 or α1,3) or G2 glycan residues, depending from the amount of terminal Gal residues (Raju, T. S., BioProcess Int. 1 (2003) 44-53). CHO type glycosylation of antibody Fc parts is e.g. described by Routier, F. H., Glycoconjugate J. 14 (1997) 201-207. Antibodies which are recombinantely expressed in non glycomodified CHO host cells usually are fucosylated at Asn297 in an amount of at least 85%. It should be understood that the term an afucosylated antibody as used herein includes an antibody having no fucose in its glycosylation pattern. It is commonly known that typical glycosylated residue position in an antibody is the asparagine at position 297 according to the EU numbering system ("Asn297").

The "EU numbering system" or "EU index" is generally used when referring to a residue in an immunoglobulin heavy chain constant region (e.g., the EU index reported in Kabat et al., Sequences of Proteins of Immunological Interest, 5th ed., Public Health Service, National Institutes of Health, Bethesda, MD (1991) expressly incorporated herein by reference).

Thus an afucosylated antibody according to the invention means an antibody of IgG1 or IgG3 isotype (preferably of IgG1 isotype) wherein the amount of fucose is 60% or less of the total amount of oligosaccharides (sugars) at Asn297 (which means that at least 40% or more of the oligosaccharides of the Fc region at Asn297 are afucosylated). In one embodiment the amount of fucose is between 40% and 60% of the oligosaccharides of the Fc region at Asn297. In another embodiment the amount of fucose is 50% or less, and in still another embodiment the amount of fucose is 30% or less of the oligosaccharides of the Fc region at Asn297. According to the invention "amount of fucose" means the amount of said oligosaccharide (fucose) within the oligosaccharide (sugar) chain at Asn297, related to the sum of all oligosaccharides (sugars) attached to Asn 297 (e.g. complex, hybrid and high mannose structures) measured by MALDI-TOF mass spectrometry and calculated as average value (for a detailed procedure to determine the amount of fucose, see e.g. WO 2008/077546). Furthermore in one embodiment, the oligosaccharides of the Fc region are bisected. The afucosylated antibody according to the invention can be expressed in a glycomodified host cell engineered to express at least one nucleic acid encoding a polypeptide having GnTIII activity in an amount sufficient to partially fucosylate the oligosaccharides in the Fc region. In one embodiment, the polypeptide having GnTIII activity is a fusion polypeptide. Alternatively α1,6-fucosyltransferase activity of the host cell can be decreased or eliminated according to U.S. Pat. No. 6,946,292 to generate glycomodified host cells. The amount of antibody fucosylation can be predetermined e.g. either by fermentation conditions (e.g. fermentation time) or by combination of at least two antibodies with different fucosylation amount. Such afucosylated antibodies and respective glycoengineering methods are described in WO 2005/044859, WO 2004/065540, WO 2007/031875, Umana, P., et al., Nature Biotechnol. 17 (1999) 176-180, WO 99/154342, WO 2005/018572, WO 2006/116260, WO 2006/114700, WO 2005/011735, WO 2005/027966, WO 97/028267, US 2006/0134709, US 2005/0054048, US 2005/0152894, WO 2003/035835, WO 2000/061739. These glycoengineered antibodies have an increased ADCC. Other glycoengineering methods yielding afucosylated antibodies according to the invention are described e.g. in Niwa, R., et al., J. Immunol. Methods 306 (2005) 151-160; Shinkawa, T., et al., J. Biol. Chem. 278 (2003) 3466-3473; WO 03/055993 or US 2005/0249722.

Thus one aspect of the invention is a type I anti-CD20 antibody, or an afucosylated anti-CD20 antibody of IgG1 or IgG3 isotype (preferably of IgG1 isotype) specifically binding to CD20 with an amount of fucose of 60% or less of the total amount of oligosaccharides (sugars) at Asn297, for the treatment of cancer in combination with a BTK inhibitor. In another aspect of the invention is the use of an afucosylated anti-CD20 antibody of IgG1 or IgG3 isotype (preferably of IgG1 isotype) specifically binding to CD20 with an amount of fucose of 60% or less of the total amount of oligosaccharides (sugars) at Asn297, for the manufacture of a medicament for the treatment of cancer in combination with a BTK inhibitor. In one embodiment, the amount of fucose is between 60% and 20% of the total amount of oligosaccharides (sugars) at Asn297. In one embodiment the amount of fucose is between 60% and 40% of the total amount of oligosaccharides (sugars) at Asn297. In one embodiment, the amount of fucose is between 0% of the total amount of oligosaccharides (sugars) at Asn297.

CD20 (also known as B-lymphocyte antigen CD20, B-lymphocyte surface antigen B1, Leu-16, Bp35, BM5, and LF5; the sequence is characterized by the SwissProt database entry P11836) is a hydrophobic transmembrane protein with a molecular weight of approximately 35 kD located on pre-B and mature B lymphocytes (Valentine, M. A. et al., J. Biol. Chem. 264 (1989) 11282-11287; Tedder, T. F., et al., Proc. Natl. Acad. Sci. U.S.A. 85 (1988) 208-212; Stamenkovic, I., et al., J. Exp. Med. 167 (1988) 1975-1980; Einfeld, D. A., et al., EMBO J. 7 (1988) 711-717; Tedder, T. F., et al., J. Immunol. 142 (1989) 2560-2568). The corresponding human gene is Membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. Alternative splicing of this gene results in two transcript variants which encode the same protein.

The terms "CD20" and "CD20 antigen" are used interchangeably herein, and include any variants, isoforms and species homologs of human CD20 which are naturally expressed by cells or are expressed on cells transfected with the CD20 gene. Binding of an antibody of the invention to the CD20 antigen mediate the killing of cells expressing CD20 (e.g., a tumor cell) by inactivating CD20. The killing of the cells expressing CD20 may occur by one or more of the following mechanisms: Cell death/apoptosis induction, ADCC and CDC.

Synonyms of CD20, as recognized in the art, include B-lymphocyte antigen CD20, B-lymphocyte surface antigen B1, Leu-16, Bp35, BM5, and LF5.

The term "anti-CD20 antibody" according to the invention is an antibody that binds specifically to CD20 antigen. Depending on binding properties and biological activities of anti-CD20 antibodies to the CD20 antigen, two types of anti-CD20 antibodies (type I and type II anti-CD20 antibodies) can be distinguished according to Cragg, M. S., et al., Blood 103 (2004) 2738-2743; and Cragg, M. S., et al., Blood 101 (2003) 1045-1052, see Table 1.

TABLE 1

Properties of type I and type II anti-CD20 antibodies

| type I anti-CD20 antibodies | type II anti-CD20 antibodies |
|---|---|
| type I CD20 epitope | type II CD20 epitope |
| Localize CD20 to lipid rafts | Do not localize CD20 to lipid rafts |
| Increased CDC (if IgG1 isotype) | Decreased CDC (if IgG1 isotype) |
| ADCC activity (if IgG1 isotype) | ADCC activity (if IgG1 isotype) |
| Full binding capacity | Reduced binding capacity |
| Homotypic aggregation | Stronger homotypic aggregation |
| Apoptosis induction upon cross-linking | Strong cell death induction without cross-linking |

Examples of type II anti-CD20 antibodies include e.g. humanized B-Ly1 antibody IgG1 (a chimeric humanized IgG1 antibody as disclosed in WO 2005/044859), 11B8 IgG1 (as disclosed in WO 2004/035607), and AT80 IgG1. Typically type II anti-CD20 antibodies of the IgG1 isotype show characteristic CDC properties. Type II anti-CD20 antibodies have a decreased CDC (if IgG1 isotype) compared to type I antibodies of the IgG1 isotype.

Examples of type I anti-CD20 antibodies include e.g. rituximab, H147 IgG3 (ECACC, hybridoma), 2C6 IgG1 (as disclosed in WO 2005/103081), 2F2 IgG1 (as disclosed and WO 2004/035607 and WO 2005/103081) and 2H7 IgG1 (as disclosed in WO 2004/056312).

The afucosylated anti-CD20 antibodies according to the invention is in one embodiment a type II anti-CD20 antibody, in another embodiment an afucosylated humanized B-Ly1 antibody.

The afucosylated anti-CD20 antibodies according to the invention have an increased antibody dependent cellular cytotoxicity (ADCC) unlike anti-CD20 antibodies having no reduced fucose.

By "afucosylated anti-CD20 antibody with increased antibody dependent cellular cytotoxicity (ADCC)" is meant an afucosylated anti-CD20 antibody, as that term is defined herein, having increased ADCC as determined by any suitable method known to those of ordinary skill in the art. One accepted in vitro ADCC assay is as follows:
1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
   i) the PBMCs are isolated using standard density centrifugation procedures and are suspended at $5 \times 10^6$ cells/ml in RPMI cell culture medium;
   ii) the target cells are grown by standard tissue culture methods, harvested from the exponential growth phase with a viability higher than 90%, washed in RPMI cell culture medium, labeled with 100 microCuries of $^{51}Cr$, washed twice with cell culture medium, and resuspended in cell culture medium at a density of $10^5$ cells/ml;
   iii) 100 microliters of the final target cell suspension above are transferred to each well of a 96-well microtiter plate;
   iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
   v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);
   vi) for the spontaneous release (SR) controls, 3 additional wells in the plate containing the labeled target cells, receive 50 microliters of RPMI cell culture medium instead of the antibody solution (point iv above);
   vii) the 96-well microtiter plate is then centrifuged at 50×g for 1 minute and incubated for 1 hour at 4° C.;
   viii) 50 microliters of the PBMC suspension (point i above) are added to each well to yield an effector: target cell ratio of 25:1 and the plates are placed in an incubator under 5% $CO_2$ atmosphere at 37° C. for 4 hours;
   ix) the cell-free supernatant from each well is harvested and the experimentally released radioactivity (ER) is quantified using a gamma counter;
   x) the percentage of specific lysis is calculated for each antibody concentration according to the formula (ER−MR)/(MR−SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);
4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress GnTIII.

Said "increased ADCC" can be obtained by glycoengineering of said antibodies, that means enhance said natural, cell-mediated effector functions of monoclonal antibodies by engineering their oligosaccharide component as described in Umana, P., et al., Nature Biotechnol. 17 (1999) 176-180 and U.S. Pat. No. 6,602,684.

The term "complement-dependent cytotoxicity (CDC)" refers to lysis of human tumor target cells by the antibody according to the invention in the presence of complement. CDC is measured preferably by the treatment of a preparation of CD20 expressing cells with an anti-CD20 antibody according to the invention in the presence of complement. CDC is found if the antibody induces at a concentration of 100 nM the lysis (cell death) of 20% or more of the tumor cells after 4 hours. The assay is performed preferably with $^{51}Cr$ or Eu labeled tumor cells and measurement of released $^{51}Cr$ or Eu. Controls include the incubation of the tumor target cells with complement but without the antibody.

The "rituximab" antibody (example of a type I anti-CD20 antibody) is a genetically engineered chimeric human gamma 1 murine constant domain containing monoclonal antibody directed against the human CD20 antigen.

The "rituximab" antibody (example of a type I anti-CD20 antibody) is a genetically engineered chimeric human gamma 1 murine constant domain containing monoclonal antibody directed against the human CD20 antigen. This chimeric antibody contains human gamma 1 constant domains and is identified by the name "C2B8" in U.S. Pat. No. 5,736,137 (Anderson et. al.) issued on Apr. 17, 1998, assigned to IDEC Pharmaceuticals Corporation. Rituximab is approved for the treatment of patients with relapsed or refracting low-grade or follicular, CD20 positive, B cell non-Hodgkin's lymphoma. In vitro mechanism of action studies have shown that rituximab exhibits human complement-dependent cytotoxicity (CDC) (Reff, M. E., et. al., Blood 83 (1994) 435-445). Additionally, it exhibits significant activity in assays that measure antibody-dependent cellular cytotoxicity (ADCC). Rituximab is not afucosylated.

TABLE 2

| Antibody | Amount of fucose |
|---|---|
| Rituximab (non-afucosylated) | >85% |
| Wild type afucosylated glyco-engineered humanized B-Ly1 (B-HH6-B-KV1) (non-afucosylated) | >85% |
| afucosylated glyco-engineered humanized B-Ly1 (B-HH6-B-KV1 GE) | 45-50% |

The term "humanized B-Ly1 antibody" refers to humanized B-Ly1 antibody as disclosed in WO 2005/044859 and WO 2007/031875, which were obtained from the murine monoclonal anti-CD20 antibody B-Ly1 (variable region of the murine heavy chain (VH): SEQ ID NO: 1; variable region of the murine light chain (VL): SEQ ID NO:2 (see Poppema, S. and Visser, L., Biotest Bulletin 3 (1987) 131-139) by chimerization with a human constant domain from IgG1 and following humanization (see WO 2005/044859 and WO 2007/031875). These "humanized B-Ly1 antibodies" are disclosed in detail in WO 2005/044859 and WO 2007/031875.

In one embodiment, the "humanized B-Ly1 antibody" has variable region of the heavy chain (VH) selected from group of of SEQ ID NO:3 to SEQ ID NO:19 (B-HH2 to B-HH9 and B-HL8 to B-HL17 of WO 2005/044859 and WO 2007/031875). In one specific embodiment, such variable domain is selected from the group consisting of SEQ ID NO:3, SEQ ID NO:4, SEQ ID NO:7, SEQ ID NO:9, SEQ ID NO:11, SEQ ID NO:13 and SEQ ID NO:15 (B-HH2, BHH-3, B-HH6, B-HH8, B-HL8, B-HL11 and B-HL13 of WO 2005/044859 and WO 2007/031875). In one specific embodiment, the "humanized B-Ly1 antibody" has variable region of the light chain (VL) of SEQ ID NO:20 (B-KV1 of WO 2005/044859 and WO 2007/031875). In one specific embodiment, the "humanized B-Ly1 antibody" has a variable region of the heavy chain (VH) of SEQ ID NO:7 (B-HH6 of WO 2005/044859 and WO 2007/031875) and a variable region of the light chain (VL) of SEQ ID NO:20 (B-KV1 of WO 2005/044859 and WO 2007/031875). Furthermore in one embodiment, the humanized B-Ly1 antibody is an IgG1 antibody. According to the invention such afucosylated humanized B-Ly1 antibodies are glycoengineered (GE) in the Fc region according to the procedures described in WO 2005/044859, WO 2004/065540, WO 2007/031875, Umana, P. et al., Nature Biotechnol. 17 (1999) 176-180 and WO 99/154342. In one embodiment, the afucosylated glyco-engineered humanized B-Ly1 is B-HH6-B-KV1 GE. In one embodiment, the anti-CD20 antibody is obinutuzumab (recommended INN, WHO Drug Information, Vol. 26, No. 4, 2012, p. 453). As used herein, obinutuzumab is synonymous for GA101. The tradename is GAZYVA. The WHO Drug Information document replaces all previous versions (e.g. Vol. 25, No. 1, 2011, p. 75-76), and is formerly known as afutuzumab (recommended INN, WHO Drug Information, Vol. 23, No. 2, 2009, p. 176; Vol. 22, No. 2, 2008, p. 124).

BTK as used herein is "Bruton's tyrosine kinase" or "Bruton agammaglobulinemia tyrosine kinase" (abbreviated Btk or BTK), which is a member of the TEC family of kinases. The BTK gene encodes the BTK protein, which is crucial for the development and maturation of B cells as mast cell activation through the high-affinity IgE receptor. The BTK gene is located on the X chromosome. More than 400 mutations of the BTK gene have been identified.

The term "BTK inhibitor" according to the invention refers to agents that prevents kinase activity of BTK with an IC50 of 0.001 µM to about 2 µM, in one embodiment with 0.002 µM to about 2 µM. In one embodiment, the BTK inhibitors are antibodies, antisense oligonucleotides, peptides.

In another embodiment, the BTK inhibitors are small molecular weight compounds with a molecular weight (MW) of less than 1500 Daltons (Da).

In one embodiment such small molecular weight BTK inhibitor compounds are the compounds described in WO2011/152351 and WO2013/081016.

In one embodiment, a small molecular weight BTK inhibitor compound according to the invention is characterized by the general formula (I)

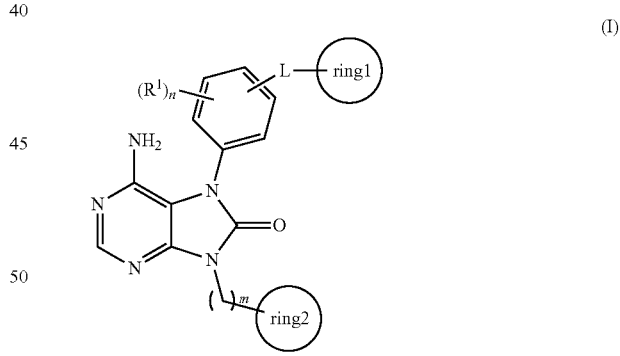

In the formula, L represents (1) —O—, (2) —S—, (3) —SO—, (4) —SO₂— (5) —NH—, (6) —C(O)—, (7) —CH₂—O—, (8) —O—CH₂—, (9) —CH₂—, or (10) —CH(OH)—;

$R^1$ represents (1) a halogen atom, (2) a $C_{1-4}$ alkyl group, (3) a $C_{1-4}$ alkoxy group, (4) a $C_{1-4}$ haloalkyl group, or (5) a $C_{1-4}$ haloalkoxy group;

ring1 represents a 4- to 7-membered cyclic group, which may be substituted by from one to five substituents each independently selected from the group consisting of (1) halogen atoms, (2) $C_{1-4}$ alkyl groups, (3) $C_{1-4}$ alkoxy groups, (4) nitrile, (5) $C_{1-4}$ haloalkyl groups, and (6) $C_{1-4}$ haloalkoxy groups, wherein when two or more substituents are present on ring1, these substituents may form a 4- to 7-membered cyclic group together with the atoms in ring1 to which these substituents are bonded;

ring2 represents a 4- to 7-membered saturated heterocycle, which may be substituted by from one to three —K—$R^2$;

K represents (1) a bond, (2) a $C_{1-4}$ alkylene, (3) —C(O)—, (4) —C(O)—$CH_2$—, (5) —$CH_2$—C(O)—, (6) —C(O)O—, or (7) —$SO_2$— (wherein the bond on the left is bonded to the ring2);

$R^2$ represents (1) a $C_{1-4}$ alkyl, (2) a $C_{2-4}$ alkenyl, or (3) a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;

$R^3$ and $R^4$ each independently represent (1) a hydrogen atom, or (2) a $C_{1-4}$ alkyl group which may be substituted by $OR^9$ or $CONR^{10}R^{11}$;

$R^3$ and $R^4$ may, together with the nitrogen atom to which they are bonded, form a 4- to 7-membered nitrogenous saturated heterocycle, which may be substituted by an oxo group or a hydroxyl group;

$R^5$ and $R^6$ each independently represent (1) a hydrogen atom, (2) a $C_{1-4}$ alkyl group, or (3) a phenyl group;

$R^7$ represents (1) a hydrogen atom or (2) a $C_{1-4}$ alkyl group;

$R^8$ represents (1) a hydrogen atom, (2) a $C_{1-4}$ alkyl group, (3) a phenyl group, or (4) a benzotriazolyl group;

$R^9$ represents (1) a hydrogen atom or (2) a $C_{1-4}$ alkyl group;

$R^{10}$ and $R^{11}$ each independently represent (1) a hydrogen atom or (2) a $C_{1-4}$ alkyl group;

n represents an integer from 0 to 4;

m represents an integer from 0 to 2; and when n is two or more, the $R^1$'s may be the same as each other or may differ from one another), an optical isomer thereof or their mixture, a salt thereof, a solvate thereof, an N-oxide thereof, or a prodrug thereof,

[2] the compound according to [1] above, wherein $R^2$ is a $C_{2-4}$ alkenyl group or a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;

[3] the compound according to [1] above, wherein ring1 is a benzene, cyclohexane, or pyridine ring, each of which may be substituted by from one to five substituents each independently selected from the group consisting of (1) halogen atoms, (2) $C_{1-4}$ alkyl groups, (3) $C_{1-4}$ alkoxy groups, (4) nitrile, and (5) $CF_3$;

[4] the compound according to [1] above, wherein ring2 is a 4- to 7-membered nitrogenous saturated heterocycle, which may be substituted by from one to three —K—$R^2$;

[5] the compound according to [4] above, wherein the 4- to 7-membered nitrogenous saturated heterocycle is an azetidine, pyrrolidine, or piperidine ring;

[6] the compound according to [1] above, represented by general formula (I-1)

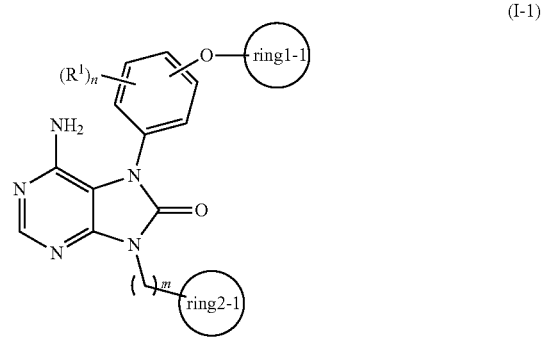

In the formula, ring1-1 represents a benzene, cyclohexane, or pyridine ring, each of which may be substituted by from one to five substituents each independently selected from the group consisting of (1) halogen atoms, (2) $C_{1-4}$ alkyl groups, (3) $C_{1-4}$ alkoxy groups, (4) nitrile, and (5) $CF_3$, and ring2-1 represents a 4- to 7-membered nitrogenous saturated heterocycle, which may be substituted by from one to three —K—$R^2$, wherein the other symbols have the same definitions as above);

[7] the compound according to [6] above, wherein $R^2$ is a $C_{2-4}$ alkenyl group or a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;

[8] the compound according to [1] above, which is (1) 9-(1-acryloyl-3-azetidinyl)-6-amino-7-(4-phenoxyphenyl)-7,9-dihydro-8H-purin-8-one, (2) 6-amino-9-{(3R)-1-[(2E)-4-(dimethylamino)-2-butenoyl]-3-pyrrolidinyl}-7-(4-phenoxyphenyl)-7,9-dihydro-8H-purin-8-one, (3) 9-[(1-acryloyl-4-piperidinyl)methyl]-6-amino-7-(4-phenoxyphenyl)-7,9-dihydro-8H-purin-8-one, (4) 6-amino-9-[(3R)-1-(2-butynoyl)-3-pyrrolidinyl]-7-(4-phenoxyphenyl)-7,9-dihydro-8H-purin-8-one, (5) 6-amino-9-{(3S)-1-[(2E)-4-(dimethylamino)-2-butenoyl]-3-pyrrolidinyl}-7-(4-phenoxyphenyl)-7,9-dihydro-8H-purin-8-one, (6) 6-amino-7-[4-(3-chlorophenoxy)phenyl]-9-{(3R)-1-[(2E)-4-(dimethylamino)-2-butenoyl]-3-pyrrolidinyl}-7,9-dihydro-8H-purin-8-one, (7) 6-amino-9-[1-(2-butynoyl)-3-pyrrolidinyl]-7-(4-phenoxyphenyl)-7,9-dihydro-8H-purin-8-one, or (8) 6-amino-9-{1-[(2E)-4-(dimethylamino)-2-butenoyl]-3-pyrrolidinyl}-7-(4-phenoxyphenyl)-7,9-dihydro-8H-purin-8-one, or an optical isomer thereof or their mixture;

Preferably, the BTK inhibitor according to the invention is 6-amino-9-[(3R)-1-(2-butynoyl)-3-pyrrolidinyl]-7-(4-phenoxyphenyl)-7,9-dihydro-8H-purin-8-one or a salt thereof.

Preparation of the BTK inhibitor according to the invention is carried out as disclosed in WO2011/152351.

"Salt" refers to salts of the compounds as a pharmaceutically acceptable salt. Such salts can be exemplified by the salts with alkali metals (potassium, sodium, and the like), salts with alkaline-earth metals (calcium, magnesium, and the like), the ammonium salt, salts with pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, and the like), and acid addition salts (inorganic acid salts (the hydrochloride, hydrobromide, hydroiodide, sulfate, phosphate, nitrate, and the like) and organic acid salts (the acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, and the like)).

"IC50" refers to the concentration of a particular compound required to inhibit 50% of a specific measured activity. IC50 of the BTK inhibitors that inhibit the BTK kinase activity can be measured, inter alia, as is described subsequently.

In Vitro Activity Assay for IC50 Determination of a BTK Inhibitor According to the Invention:

The Btk enzyme inhibitory activity was measured, based on the protocol provided by the manufacturer, using Btk (Invitrogen Corporation) and the Z'-LYTE™ Kinase Assay Kit-Tyr1 peptide (Invitrogen Corporation), which contained the following reagents: Tyr-1 peptide, Thy-1 phosphopeptide, 5× kinase buffer, ATP, development reagent B, development buffer, and stop reagent. 5 µL/well of a solution of a BTK inhibitor diluted with dimethyl sulfoxide (DMSO), or DMSO, and 10 µL/well of the substrate/enzyme mixture solution were dispensed to a 96-well assay plate and a reaction was carried out for 20 minutes at 30° C. The substrate/enzyme mixture solution was prepared by dilution with the kinase buffer (DL-dithiothreitol (DTT, 2.7 mM), 1.33× kinase buffer) to provide a final concentration for the Tyr-1 peptide of 4 µM and a final Btk concentration of 5 nM. 5 µL/well of the adenosine triphosphate (ATP, final concentration=36 µM) was then added and a reaction was carried out for 1 hour at 30° C. After the completion of the reaction, 10 µL of a development solution, provided by diluting the development reagent B to 128× using the development buffer, was added and a reaction was carried out for an additional 1 hour at 30° C. The enzymatic reaction was then stopped by adding 10 µL of the stop solution. The fluorescence intensity at 445 nm and 520 nm in each well was measured using a Fusion Universal Microplate Analyzer (PerkinElmer Inc.) fluorescence plate reader. The percent phosphorylation was determined using the ratio of the emission at 445 nm (coumarin emission) to the emission at 520 nm (fluorescein emission) in accordance with the protocol provided with the kit.

The percent inhibition (%) by a BTK inhibitor was calculated using the following equation.

percent inhibition (%) of phosphorylation=
1−{(AC−AX)/(AC−AB)}×100

AX: % phosphorylation when a BTK inhibitor has been added

AB: % phosphorylation in the absence of ATP addition (blank)

AC: % phosphorylation when only DMSO has been added (control)

The 50% inhibition value (IC50 value) for a BTK inhibitor was determined from the inhibition curve based on the % inhibition at each concentration of a BTK inhibitor.

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions (Jenkins, N., et al., Nature Biotechnol. 14 (1996) 975-981).

Mammalian cells are the excellent hosts for production of therapeutic glycoproteins, due to their capability to glycosylate proteins in the most compatible form for human application (Cumming, D. A., et al., Glycobiology 1 (1991) 115-130; Jenkins, N., et al., Nature Biotechnol. 14 (1996) 975-981). Bacteria very rarely glycosylate proteins, and like other types of common hosts, such as yeasts, filamentous fungi, insect and plant cells, yield glycosylation patterns associated with rapid clearance from the blood stream, undesirable immune interactions, and in some specific cases, reduced biological activity. Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serum free media, and permit the development of safe and reproducible bioprocesses. Other commonly used animal cells include baby hamster kidney (BHK) cells, NS0– and SP2/0-mouse myeloma cells. More recently, production from transgenic animals has also been tested (Jenkins, N., et al., Nature Biotechnol. 14 (1996) 975-981).

All antibodies contain carbohydrate structures at conserved positions in the heavy chain constant regions, with each isotype possessing a distinct array of N-linked carbohydrate structures, which variably affect protein assembly, secretion or functional activity (Wright, A., and Morrison, S. L., Trends Biotech. 15 (1997) 26-32). The structure of the attached N-linked carbohydrate varies considerably, depending on the degree of processing, and can include high-mannose, multiply-branched as well as biantennary complex oligosaccharides (Wright, A., and Morrison, S. L., Trends Biotech. 15 (1997) 26-32). Typically, there is heterogeneous processing of the core oligosaccharide structures attached at a particular glycosylation site such that even monoclonal antibodies exist as multiple glycoforms. Likewise, it has been shown that major differences in antibody glycosylation occur between cell lines, and even minor differences are seen for a given cell line grown under different culture conditions (Lifely, M. R., et al., Glycobiology 5 (1995) 813-822).

One way to obtain large increases in potency, while maintaining a simple production process and potentially avoiding significant, undesirable side effects, is to enhance the natural, cell-mediated effector functions of monoclonal antibodies by engineering their oligosaccharide component as described in Umana, P. et al., Nature Biotechnol. 17 (1999) 176-180 and U.S. Pat. No. 6,602,684. IgG1 type antibodies, the most commonly used antibodies in cancer immunotherapy, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol. Rev. 163 (1998) 59-76; Wright, A. and Morrison, S. L., Trends Biotechnol. 15 (1997) 26-32).

It was previously shown that overexpression in Chinese hamster ovary (CHO) cells of ß(1,4)-N-acetylglucosaminyltransferase III ("GnTIII7y), a glycosyltransferase catalyzing the formation of bisected oligosaccharides, significantly increases the in vitro ADCC activity of an antineuroblastoma chimeric monoclonal antibody (chCE7) produced by the engineered CHO cells (see Umana, P. et al., Nature Biotechnol. 17 (1999) 176-180; and WO 99/154342, the entire contents of which are hereby incorporated by reference). The antibody chCE7 belongs to a large class of unconjugated monoclonal antibodies which have high tumor affinity and specificity, but have too little potency to be clinically useful when produced in standard industrial cell lines lacking the GnTIII enzyme (Umana, P., et al., Nature Biotechnol. 17 (1999) 176-180). That study was the first to show that large increases of ADCC activity could be obtained by engineering the antibody producing cells to express GnTIII, which also led to an increase in the proportion of constant region (Fc)-associated, bisected oligosaccharides, including bisected, non-fucosylated oligosaccharides, above the levels found in naturally-occurring antibodies.

The term "cancer" as used herein includes lymphomas, lymphocytic leukemias, lung cancer, non small cell lung (NSCL) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymomas, medulloblastomas, meningiomas, squamous cell carcinomas, pituitary adenoma, including refractory versions of any of the above cancers, or a combination of one or more of the above cancers. In one embodiment, the term cancer refers to a CD20 expressing cancer.

The term "expression of the CD20" antigen is intended to indicate an significant level of expression of the CD20 antigen in a cell, preferably on the cell surface of a T- or B-cell, more preferably a B-cell, from a tumor or cancer, respectively, preferably a non-solid tumor. Patients having a "CD20 expressing cancer" can be determined by standard assays known in the art. For example CD20 antigen expression can be measured using immunohistochemical (IHC) detection, FACS or via PCR-based detection of the corresponding mRNA.

The term "CD20 expressing cancer" as used herein refers to all cancers in which the cancer cells show an expression of the CD20 antigen. Preferably CD20 expressing cancer as used herein refers to lymphomas (preferably B-Cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma), c) marginal zone lymphomas (including extranodal marginal zone B cell lymphoma (Mucosa-associated lymphatic tissue lymphomas, MALT), nodal marginal zone B cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma), f) hairy cell leukemia, g) lymphocytic lymphoma, waldenstrom's macroglobulinemia, h) acute lymphocytic leukemia (ALL), chronic lymphocytic leukemia (CLL)/small lymphocytic lymphoma (SLL), B-cell prolymphocytic leukemia, i) plasma cell neoplasms, plasma cell myeloma, multiple myeloma, plasmacytoma, j) Hodgkin's disease.

In one embodiment, the CD20 expressing cancer is a B-Cell Non-Hodgkin's lymphomas (NHL). In another embodiment, the CD20 expressing cancer is a Mantle cell lymphoma (MCL), acute lymphocytic leukemia (ALL), chronic lymphocytic leukemia (CLL), B-cell diffuse large cell lymphoma (DLCL), Burkitt's lymphoma, hairy cell leukemia, follicular lymphoma, multiple myeloma, marginal zone lymphoma, post transplant lymphoproliferative disorder (PTLD), HIV associated lymphoma, waldenstrom's macroglobulinemia, or primary CNS lymphoma.

The term "a method of treating", "a method of treatment" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed to induce an overall beneficial course of action.

The terms "combination", "co-administration" or "co-administering" refer to the administration of said type I anti-CD20 antibody or said afucosylated anti-CD20, and said BTK inhibitor as two separate formulations (or as one single formulation). The co-administration can be simultaneous or sequential in either order, wherein preferably there is a time period while both (or all) active agents simultaneously exert their biological activities. Said type I anti-CD20 antibody or said anti-CD20 afucosylated antibody and said BTK inhibitor are co-administered either simultaneously or sequentially (e.g. intravenous (i.v.) through a continuous infusion (one for the anti-CD20 antibody and eventually one for said BTK inhibitor; or e.g. the anti-CD20 antibody is administered intravenous (i.v.) through a continuous infusion and said BTK inhibitor is administered orally). When both therapeutic agents are co-administered sequentially, the dose is administered either on the same day in two separate administrations, or one of the agents is administered on day 1 and the second is co-administered on day 2 to day 7, preferably on day 2 to 4. Thus in one embodiment the term "sequentially" means within 7 days after the dose of the first component (anti-CD20 antibody or BTK inhibitor), preferably within 4 days after the dose of the first component; and the term "simultaneously" means at the same time. The terms "co-administration" with respect to the maintenance doses of said type I anti-CD20 antibody or said afucosylated anti-CD20 antibody and said BTK inhibitor mean that the maintenance doses can be either co-administered simultaneously, if the treatment cycle is appropriate for both drugs, e.g. every week. Or BTK inhibitor is administered e.g. every first to third day and said afucosylated antibody is administered every week. Or the maintenance doses are co-administered sequentially, either within one or within several days.

It is self-evident that the antibodies are administered to the patient in a "therapeutically effective amount" (or simply "effective amount") which is the amount of the respective compound or combination that will elicit the biological or medical response of a tissue, system, animal or human that is being sought by the researcher, veterinarian, medical doctor or other clinician.

The amount of co-administration of said type I anti-CD20 antibody or said anti-CD20 afucosylated antibody and said BTK inhibitor and the timing of co-administration will depend on the type (species, gender, age, weight, etc.) and condition of the patient being treated and the severity of the disease or condition being treated. Said type I anti-CD20 antibody or said afucosylated anti-CD20 antibody and said BTK inhibitor are suitably co-administered to the patient at one time or over a series of treatments e.g. on the same day or on the day after.

If the administration is intravenous the initial infusion time for said type I anti-CD20 antibody, said afucosylated anti-CD20 antibody or said BTK inhibitor may be longer than subsequent infusion times, for instance approximately 90 minutes for the initial infusion, and approximately 30 minutes for subsequent infusions (if the initial infusion is well tolerated).

Depending on the type and severity of the disease, about 0.1 mg/kg to 50 mg/kg (e.g. 0.1-20 mg/kg) of said type I anti-CD20 antibody or afucosylated anti-CD20 antibody; and 1 µg/kg to 50 mg/kg (e.g. 0.1-20 mg/kg) of said BTK inhibitor is an initial candidate dosage for co-administration of both drugs to the patient. In one embodiment the preferred dosage of said afucosylated anti-CD20 antibody (preferably the afucosylated humanized B-Ly1 antibody, more preferably obinutuzumab) will be in the range from about 0.05 mg/kg to about 30 mg/kg. Thus, one or more doses of about 0.5 mg/kg, 2.0 mg/kg, 4.0 mg/kg, 10 mg/kg or 30 mg/kg (or any combination thereof) may be co-administered to the patient. In one embodiment the preferred dosage of said BTK inhibitor (preferably 6-amino-9-[(3R)-1-(2-butynoyl)-3-pyrrolidinyl]-7-(4-phenoxyphenyl)-7,9-dihydro-8H-purin-8-one or a salt thereof) will be in the range from about 0.05 mg/kg to about 30 mg/kg. Thus, one or more doses of about 0.5 mg/kg, 2.0 mg/kg, 4.0 mg/kg, 10 mg/kg or 30 mg/kg (or any combination thereof) may be co-administered to the patient.

Depending on the type (species, gender, age, weight, etc.) and condition of the patient and on the type I anti-CD20 antibody, preferably rituximub or type of afucosylated anti-CD20 antibody, preferably the afucosylated humanized B-Ly1 antibody, more preferably obinutuzumab, the dosage and the administration schedule of said type I anti-CD20 antibody or said afucosylated anti-CD20 antibody can differ from said BTK inhibitor. E.g. the the type I anti-CD20 antibody or said afucosylated anti-CD20 antibody may be administered e.g. every one to three weeks and said BTK inhibitor may be administered daily or every 2 to 10 days. An initial higher loading dose, followed by one or more lower doses may also be administered.

In one embodiment the preferred dosage of type I anti-CD20 antibody (preferably rituximab) will be in the range from about 100 mg/m$^2$ to about 1000 mg/m$^2$ on day 1, 8, 15, 22, 29, 36, 43, 50, 57 of a 8-weeks-dosage-cycle.

In one embodiment the preferred dosage of said afucosylated anti-CD20 antibody (preferably the afucosylated humanized B-Ly1 antibody, more preferably obinutuzumab) will be 800 to 1600 mg (in on embodiment 800 to 1200 mg) on day 1, 8, 15 of a 3- to 6-weeks-dosage-cycle and then in a dosage of 400 to 1200 (in one embodiment 800 to 1200 mg on day 1 of up to nine 3- to 4-weeks-dosage-cycles.

In one embodiment the dose for said BTK inhibitor selected from the group consisting of: (1) 9-(1-acryloyl-3-azetidinyl)-6-amino-7-(4-phenoxyphenyl)-7,9-dihydro-8H-purin-8-one, (2) 6-amino-9-{(3R)-1-[(2E)-4-(dimethylamino)-2-butenoyl]-3-pyrrolidinyl}-7-(4-phenoxyphenyl)-7,9-dihydro-8H-purin-8-one, (3) 9-[(1-acryloyl-4-piperidinyl)methyl]-6-amino-7-(4-phenoxyphenyl)-7,9-dihydro-8H-purin-8-one, (4) 6-amino-9-[(3R)-1-(2-butynoyl)-3-pyrrolidinyl]-7-(4-phenoxyphenyl)-7,9-dihydro-8H-purin-8-one, (5) 6-amino-9-{(3S)-1-[(2E)-4-(dimethylamino)-2-butenoyl]-3-pyrrolidinyl}-7-(4-phenoxyphenyl)-7,9-dihydro-8H-purin-8-one, (6) 6-amino-7-[4-(3-chlorophenoxy)phenyl]-9-{(3R)-1-[(2E)-4-(dimethylamino)-2-butenoyl]-3-pyrrolidinyl}-7,9-dihydro-8H-purin-8-one, (7) 6-amino-9-[1-(2-butynoyl)-3-pyrrolidinyl]-7-(4-phenoxyphenyl)-7,9-dihydro-8H-purin-8-one, and (8) 6-amino-9-{1-[(2E)-4-(dimethylamino)-2-butenoyl]-3-pyrrolidinyl}-7-(4-phenoxyphenyl)-7,9-dihydro-8H-purin-8-one is as follows. The dose for said BTK inhibitor selected from the group of an optical isomer of said compounds (1) to (8) and the mixture thereof is as follows. The dose for said BTK inhibitor 6-amino-9-[(3R)-1-(2-butynoyl)-3-pyrrolidinyl]-7-(4-phenoxyphenyl)-7,9-dihydro-8H-purin-8-one or a salt thereof is as follows. Said dose according to the invention is 10 mg/kg to 70 mg/kg, preferably 20 mg/kg to 55 mg/kg, once daily or every other day as oral administration.

The recommended dose may vary whether there is a further co-administration of chemotherapeutic agent and based on the type of chemotherapeutic agent.

In a embodiment, this invention is useful for preventing or reducing metastasis or further dissemination in such a patient suffering from cancer, preferably CD20 expressing cancer. This invention is useful for increasing the duration of survival of such a patient, increasing the progression free survival of such a patient, increasing the duration of response, resulting in a statistically significant and clinically meaningful improvement of the treated patient as measured by the duration of survival, progression free survival, response rate or duration of response. In a preferred embodiment, this invention is useful for increasing the response rate in a group of patients.

In the context of this invention, additional other cytotoxic, chemotherapeutic or anti-cancer agents, or compounds or ionizing radiation that enhance the effects of such agents (e.g. cytokines) may be used in the type I anti-CD20 antibody or the afucosylated anti-CD20 antibody and said BTK inhibitor combination treatment of cancer. Such molecules are suitably present in combination in amounts that are effective for the purpose intended. In one embodiment, said type I anti-CD20 antibody, preferably rituximab or said afucosylated anti-CD20 antibody, preferably the afucosylated humanized B-Ly1 antibody, more preferably obinutuzumab, and said BTK inhibitor combination treatment is used without such additional cytotoxic, chemotherapeutic or anti-cancer agents, or compounds that enhance the effects of such additional agents.

Such additional agents include, for example: alkylating agents or agents with an alkylating action, such as cyclophosphamide (CTX; e.g. Cytoxan®), chlorambucil (CHL; e.g. Leukeran®), cisplatin (CisP; e.g. Platinol®) busulfan (e.g. Myleran®), melphalan, carmustine (BCNU), streptozotocin, triethylenemelamine (TEM), mitomycin C, and the like; anti-metabolites, such as methotrexate (MTX), etoposide (VP16; e.g. Vepesid®), 6-mercaptopurine (6MP), 6-thioguanine (6TG), cytarabine (Ara-C), 5-fluorouracil (5-FU), capecitabine (e.g. Xeloda®), dacarbazine (DTIC), and the like; antibiotics, such as actinomycin D, doxorubicin (DXR; e.g. Adriamycin®), daunorubicin (daunomycin), bleomycin, mithramycin and the like; alkaloids, such as *vinca* alkaloids such as vincristine (VCR), vinblastine, and the like; and other antitumor agents, such as paclitaxel (e.g. Taxol®) and paclitaxel derivatives, the cytostatic agents, glucocorticoids such as dexamethasone (DEX; e.g. Decadron®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: amifostine (e.g. Ethyol®), dactinomycin, mechlorethamine (nitrogen mustard), streptozocin, cyclophosphamide, lomustine (CCNU), doxorubicin lipo (e.g. Doxil®), gemcitabine (e.g. Gemzar®), daunorubicin lipo (e.g. Daunoxome®), procarbazine, mitomycin, docetaxel (e.g. Taxotere®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil. In one embodiment, the afucosylated anti-CD20 antibody and said BTK inhibitor combination treatment is used without such additional agents.

The use of the cytotoxic and anticancer agents described above as well as antiproliferative target-specific anticancer drugs like protein kinase inhibitors in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

In the context of this invention, an effective amount of ionizing radiation may be carried out and/or a radiopharmaceutical may be used in addition to the type I anti-CD20 antibody or the afucosylated anti-CD20 antibody and said BTK inhibitor combination treatment of CD20 expressing cancer. The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, yttrium-90, cesium-137, iridium-192, americium-241, gold-198, cobalt-57, copper-67, technetium-99, iodine-123, iodine-131, and indium-111. Is also possible to label the antibody with such radioactive isotopes. In one embodiment, the type I anti-CD20 antibody or the afucosylated anti-CD20 antibody and said BTK inhibitor combination treatment is used without such ionizing radiation.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in WO 99/60023.

The type I anti-CD20 antibody or the afucosylated anti-CD20 antibodies are administered to a patient according to known methods, by intravenous administration as a bolus or by continuous infusion over a period of time, by intramuscular, intraperitoneal, intracerobrospinal, subcutaneous, intra-articular, intrasynovial, or intrathecal routes. In one embodiment, the administration of the antibody is intravenous or subcutaneous.

The BTK inhibitor is administered to a patient according to known methods, by intravenous administration as a bolus or by continuous infusion over a period of time, orally, by intramuscular, intraperitoneal, intracerobrospinal, subcutaneous, intra-articular, intrasynovial, or intrathecal routes. In one embodiment, the administration of the BTK inhibitor is intravenous or orally.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Pharmaceutical Compositions:

Pharmaceutical compositions can be obtained by processing the anti-CD20 antibody and/or the BTK inhibitor according to this invention with pharmaceutically acceptable, inorganic or organic carriers. Lactose, corn starch or derivatives thereof, talc, stearic acids or it's salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

In one embodiment of the invention the composition comprises both said type I anti-CD20 antibody (preferably rituximab) or said afucosylated anti-CD20 antibody with an amount of fucose is 60% or less (preferably the afucosylated humanized B-Ly1 antibody, more preferably obinutuzumab) and said BTK inhibitor for use in the treatment of cancer, in particular of CD20 expressing cancer (preferably a lymphoma or lymphocytic leukemia, more preferably a B-Cell Non-Hodgkin's lymphoma (NHL), Mantle cell lymphoma (MCL), acute lymphocytic leukemia (ALL), chronic lymphocytic leukemia (CLL), B-cell diffuse large cell lymphoma (DLCL), Burkitt's lymphoma, hairy cell leukemia, follicular lymphoma, multiple myeloma, marginal zone lymphoma, post transplant lymphoproliferative disorder (PTLD), HIV associated lymphoma, waldenstrom's macroglobulinemia, or primary CNS lymphoma).

Said pharmaceutical composition may further comprise one or more pharmaceutically acceptable carriers.

The present invention further provides a pharmaceutical composition, e.g. for use in cancer, comprising (i) an effective first amount of a type I anti-CD20 antibody (preferably rituximab) or an afucosylated anti-CD20 antibody with an amount of fucose is 60% or less (preferably an afucosylated humanized B-Ly1 antibody), and (ii) an effective second amount of a BTK inhibitor. Such composition optionally comprises pharmaceutically acceptable carriers and/or excipients.

Pharmaceutical compositions of the type I anti-CD20 antibody or the afucosylated anti-CD20 antibody alone used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. (ed.) (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Pharmaceutical compositions of BTK inhibitors can be similar to those described above for the type I anti-CD20 antibody or the afucosylated anti-CD20 antibody.

Pharmaceutical compositions of small molecule BTK inhibitor include those suitable for oral, nasal, topical (including buccal and sublingual), rectal, vaginal and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a BTK inhibitor which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent. Methods of preparing these compositions include the step of bringing into association a BTK inhibitor with the carrier and, optionally, one or more accessory ingredients. In general, the pharmaceutical compositions of the BTK inhibitor are prepared by uniformly and intimately bringing into association a BTK inhibitor with liquid carriers, or finely divided solid carriers, or both, and then, if necessary, shaping the product. Pharmaceutical compositions suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a BTK inhibitor as an active ingredient. A BTK inhibitor may also be administered as a bolus, electuary or paste.

In one further embodiment of the invention, the type I anti-CD20 antibody or the afucosylated anti-CD20 antibody and the BTK inhibitor are formulated into two separate pharmaceutical compositions.

The active ingredients may also be entrapped in microcapsules prepared, for example, by coacervation techniques or by interracial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

One embodiment is a pharmaceutical composition comprising a combination of a type I anti-CD20 antibody or a humanized B-Ly1 antibody which is afucosylated with an amount of fucose of 60% or less of the total amount of oligosaccharides (sugars) at Asn297, and 6-amino-9-[(3R)-1-(2-butynoyl)-3-pyrrolidinyl]-7-(4-phenoxyphenyl)-7,9-dihydro-8H-purin-8-one or a salt thereof, for the treatment of cancer.

The present invention further provides a method for the treatment of cancer, comprising administering to a patient in need of such treatment (i) an effective first amount of a type I anti-CD20 antibody or an afucosylated anti-CD20 antibody with an amount of fucose is 60% or less, (preferably an afucosylated humanized B-Ly1 antibody); and (ii) an effective second amount of a BTK inhibitor.

In one embodiment, the amount of fucose of is between 40% and 60%.

Preferably, said cancer is a CD20 expressing cancer.

Preferably, said CD20 expressing cancer is a lymphoma or lymphocytic leukemia.

Preferably, type I anti-CD20 antibody is rituximab.

Preferably, said afucosylated anti-CD20 antibody is a type II anti-CD20 antibody.

Preferably, said antibody is a humanized B-Ly1 antibody as disclosed herein.

Preferably, said antibody is obinutuzumab.

Preferably, said BTK inhibitor is selected from the group consisting of: (1) 9-(1-acryloyl-3-azetidinyl)-6-amino-7-(4-phenoxyphenyl)-7,9-dihydro-8H-purin-8-one, (2) 6-amino-9-{(3R)-1-[(2E)-4-(dimethylamino)-2-butenoyl]-3-pyrrolidinyl)}-7-(4-phenoxyphenyl)-7,9-dihydro-8H-purin-8-one, (3) 9-[(1-acryloyl-4-piperidinyl)methyl]-6-amino-7-(4-phenoxyphenyl)-7,9-dihydro-8H-purin-8-one, (4) 6-amino-9-[(3R)-1-(2-butynoyl)-3-pyrrolidinyl]-7-(4-phenoxyphenyl)-7,9-dihydro-8H-purin-8-one, (5) 6-amino-9-{(3S)-1-[(2E)-4-(dimethylamino)-2-butenoyl]-3-pyrrolidinyl}-7-(4-phenoxyphenyl)-7,9-dihydro-8H-purin-8-one, (6) 6-amino-7-[4-(3-chlorophenoxy)phenyl]-9-{(3R)-1-[(2E)-4-(dimethylamino)-2-butenoyl]-3-pyrrolidinyl}-7,9-dihydro-8H-purin-8-one, (7) 6-amino-9-[1-(2-butynoyl)-3-pyrrolidinyl]-7-(4-phenoxyphenyl)-7,9-dihydro-8H-purin-8-one, and (8) 6-amino-9-{1-[(2E)-4-(dimethylamino)-2-butenoyl]-3-pyrrolidinyl}-7-(4-phenoxyphenyl)-7,9-dihydro-8H-purin-8-one.
Also preferably, said BTK inhibitor is selected from the group of an optical isomer of said compounds (1) to (8) and the mixture thereof.

Preferably, said BTK inhibitor is 6-amino-9-[(3R)-1-(2-butynoyl)-3-pyrrolidinyl]-7-(4-phenoxyphenyl)-7,9-dihydro-8H-purin-8-one or a salt thereof.

Preferably, said salt is a hydrochloride.

Preferably, said type I anti-CD20 antibody is rituximab or said afucosylated anti-CD20 antibody is a humanized B-Ly1 antibody and said BTK inhibitor is selected from the group consisting of: (1) 9-(1-acryloyl-3-azetidinyl)-6-amino-7-(4-phenoxyphenyl)-7,9-dihydro-8H-purin-8-one, (2) 6-amino-9-{(3R)-1-[(2E)-4-(dimethylamino)-2-butenoyl]-3-pyrrolidinyl}-7-(4-phenoxyphenyl)-7,9-dihydro-8H-purin-8-one, (3) 9-[(1-acryloyl-4-piperidinyl)methyl]-6-amino-7-(4-phenoxyphenyl)-7,9-dihydro-8H-purin-8-one, (4) 6-amino-9-[(3R)-1-(2-butynoyl)-3-pyrrolidinyl]-7-(4-phenoxyphenyl)-7,9-dihydro-8H-purin-8-one, (5) 6-amino-9-{(3S)-1-[(2E)-4-(dimethylamino)-2-butenoyl]-3-pyrrolidinyl}-7-(4-phenoxyphenyl)-7,9-dihydro-8H-purin-8-one, (6) 6-amino-7-[4-(3-chlorophenoxy)phenyl]-9-{(3R)-1-[(2E)-4-(dimethylamino)-2-butenoyl]-3-pyrrolidinyl}-7,9-dihydro-8H-purin-8-one, (7) 6-amino-9-[1-(2-butynoyl)-3-pyrrolidinyl]-7-(4-phenoxyphenyl)-7,9-dihydro-8H-purin-8-one, and (8) 6-amino-9-{1-[(2E)-4-(dimethylamino)-2-butenoyl]-3-pyrrolidinyl}-7-(4-phenoxyphenyl)-7,9-dihydro-8H-purin-8-one. Also preferably, said BTK inhibitor is selected from the group of an optical isomer of said compounds (1) to (8) and the mixture thereof. Preferably, said BTK inhibitor is 6-amino-9-[(3R)-1-(2-butynoyl)-3-pyrrolidinyl]-7-(4-phenoxyphenyl)-7,9-dihydro-8H-purin-8-one or a salt thereof and said cancer is a CD20 expressing cancer, preferably a lymphoma or lymphocytic leukemia.

As used herein, the term "patient" preferably refers to a human in need of treatment with a type I anti-CD20 antibody or an afucosylated anti-CD20 antibody (e.g. a patient suffering from CD20 expressing cancer) for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others.

The present invention further comprises a type I anti-CD20 antibody or an afucosylated anti-CD20 antibody with an amount of fucose is 60% or less, and a BTK inhibitor for use in the treatment of cancer.

Preferably, said type I anti-CD20 antibody is rituximab.

Preferably, said afucosylated anti-CD20 antibody is a humanized B-Ly1 antibody.

Preferably, said afucosylated humanized B-Ly1 antibody is obinutuzumab.

Preferably, said BTK inhibitor is selected from the group consisting of: (1) 9-(1-acryloyl-3-azetidinyl)-6-amino-7-(4-phenoxyphenyl)-7,9-dihydro-8H-purin-8-one, (2) 6-amino-9-{(3R)-1-[(2E)-4-(dimethylamino)-2-butenoyl]-3-pyrrolidinyl)}-7-(4-phenoxyphenyl)-7,9-dihydro-8H-purin-8-one, (3) 9-[(1-acryloyl-4-piperidinyl)methyl]-6-amino-7-(4-phenoxyphenyl)-7,9-dihydro-8H-purin-8-one, (4) 6-amino-9-[(3R)-1-(2-butynoyl)-3-pyrrolidinyl]-7-(4-phenoxyphenyl)-7,9-dihydro-8H-purin-8-one, (5) 6-amino-9-{(3S)-1-[(2E)-4-(dimethylamino)-2-butenoyl]-3-pyrrolidinyl}-7-(4-phenoxyphenyl)-7,9-dihydro-8H-purin-8-one, (6) 6-amino-7-[4-(3-chlorophenoxy)phenyl]-9-{(3R)-1-[(2E)-4-(dimethylamino)-2-butenoyl]-3-pyrrolidinyl)}-7,9-dihydro-8H-purin-8-one, (7) 6-amino-9-[1-(2-butynoyl)-3-pyrrolidinyl]-7-(4-phenoxyphenyl)-7,9-dihydro-8H-purin-8-one, and (8) 6-amino-9-{1-[(2E)-4-(dimethylamino)-2-butenoyl]-3-pyrrolidinyl}-7-(4-phenoxyphenyl)-7,9-dihydro-8H-purin-8-one. Also preferably, said BTK inhibitor is selected from the group of an optical isomer of said compounds (1) to (8) and the mixture thereof.

Preferably, said BTK inhibitor is 6-amino-9-[(3R)-1-(2-butynoyl)-3-pyrrolidinyl]-7-(4-phenoxyphenyl)-7,9-dihydro-8H-purin-8-one or a salt thereof. Said compound is also shown as the following structure:

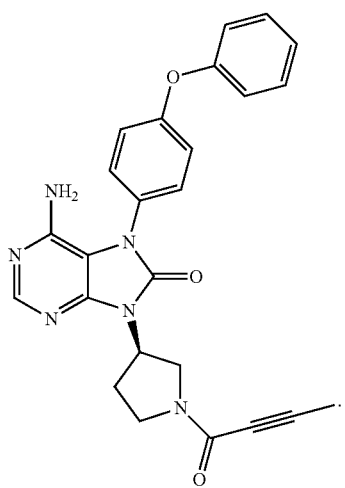 [SMILES: CC#CC(=O)N1CC[C@@H](n2c(=O)n(-c3ccc(Oc4ccccc4)cc3)c3c(N)ncnc32)C1]

Preferably, said salt is a hydrochloride.

Preferably, said type I anti-CD20 antibody is rituximab or said afucosylated anti-CD20 antibody is a humanized B-Ly1 antibody, more preferably obinutuzumab, and said BTK inhibitor is selected from the group consisting of: (1) 9-(1-acryloyl-3-azetidinyl)-6-amino-7-(4-phenoxyphenyl)-7,9-dihydro-8H-purin-8-one, (2) 6-amino-9-{(3R)-1-[(2E)-4-(dimethylamino)-2-butenoyl]-3-pyrrolidinyl}-7-(4-phenoxyphenyl)-7,9-dihydro-8H-purin-8-one, (3) 9-[(1-acryloyl-4-piperidinyl)methyl]-6-amino-7-(4-phenoxyphenyl)-7,9-dihydro-8H-purin-8-one, (4) 6-amino-9-[(3R)-1-(2-butynoyl)-3-pyrrolidinyl]-7-(4-phenoxyphenyl)-7,9-dihydro-8H-purin-8-one, (5) 6-amino-9-{(3S)-1-[(2E)-4-(dimethylamino)-2-butenoyl]-3-pyrrolidinyl)}-7-(4-phenoxyphenyl)-7,9-dihydro-8H-purin-8-one, (6) 6-amino-7-[4-(3-chlorophenoxy)phenyl]-9-{(3R)-1-[(2E)-4-(dimethylamino)-2-butenoyl]-3-pyrrolidinyl)}-7,9-dihydro-8H-purin-8-one, (7) 6-amino-9-[1-(2-butynoyl)-3-pyrrolidinyl]-7-(4-phenoxyphenyl)-7,9-dihydro-8H-purin-8-one, and (8) 6-amino-9-{1-[(2E)-4-(dimethylamino)-2-butenoyl]-3-pyrrolidinyl}-7-(4-phenoxyphenyl)-7,9-dihydro-8H-purin-8-one. Also preferably, said BTK inhibitor is selected from the group of an optical isomer of said compounds (1) to (8) and the mixture thereof. Preferably, said BTK inhibitor is 6-amino-9-[(3R)-1-(2-butynoyl)-3-pyrrolidinyl]-7-(4-phenoxyphenyl)-7,9-dihydro-8H-purin-8-one or a salt thereof, and said cancer is a CD20 expressing cancer, preferably a lymphoma or lymphocytic leukemia.

The following examples and figures are provided to aid the understanding of the present invention, the true scope of which is set forth in the appended claims. It is understood that modifications can be made in the procedures set forth without departing from the spirit of the invention.

Sequence Listing

SEQ ID NO: 1 amino acid sequence of variable region of the heavy chain (VH) of murine monoclonal anti-CD20 antibody B-Ly1.

SEQ ID NO: 2 amino acid sequence of variable region of the light chain (VL) of murine monoclonal anti-CD20 antibody B-Ly1.

SEQ ID NO: 3-19 amino acid sequences of variable region of the heavy chain (VH) of humanized B-Ly1 antibodies (B-HH2 to B-HH9, B-HL8, and B-HL10 to B-HL17)

SEQ ID NO: 20 amino acid sequences of variable region of the light chain (VL) of humanized B-Ly1 antibody B-KV1

EXPERIMENTAL PROCEDURES

Example 1

Antitumor efficacy study of BTK inhibitor in combination with anti-CD20 Abs in SCID mice subcutaneously xenografted with TMD8 (ABC-DLBCL) cells 1. Materials and Methods 1.1. Test Substances The test substance, 6-amino-9-[(3R)-1-(2-butynoyl)-3-pyrrolidinyl]-7-(4-phenoxyphenyl)-7,9-dihydro-8H-purin-8-one hydrochloride (hereinafter referred to as "compound A"), was stored in sealed containers at ambient temperature, protected from light.

GA101 (obinutuzumab, sold under the tradename Gazyva® or Gazyvaro®): 500 mg, Rituximab (RTX, sold under the tradenames Rituxan® and MabThera®): 200 mg, were supplied by Roche Glycart AG, and stored at 4° C.

1.2. Substance Vehicle

Compound A was weighed out and suspended in a 0.5 w/v % methyl cellulose 400 cP solution (Wako Pure Chemical Industries, Ltd., hereinafter referred to as "0.5% MC"), using a mortar and pestle, to obtain a 1 mg/mL suspension. The suspension was used within 7 days of preparation. The suspension was confirmed to be stable and uniform for 7 days under refrigeration, protected from light, and for a further 24 hours at ambient temperature exposed to indoor lighting.

The stock solutions of both GA101 (25 mg/mL) and Rituximab (10 mg/mL) were kept at 4° C. Before administration to mice, the stock solutions were diluted in NaCl 0.9% at 0.3, 1 and 3 mg/ml for dose finding study and at 0.1 mg/ml and 0.3 mg/ml for the combination study.

1.3. Route of Drug Administration

Compound A was per os (PO) administered to mice twice daily by oral gavage via a disposable oral feeding needle (Fuchigami Kikai Co.) at 10 ml/kg. GA101/Rituximab were intravenously (IV) injected at 10 ml/kg in the caudal vein of mice. For all treatments, the administration volumes were adapted according to the closest measure of individual body weight for each mouse. The compound A b.i.d. group and the vehicle group received compound A and 0.5% MC, respectively, in the morning and afternoon at an interval of 8 h or more.

2. Animals

Female C.B-17/lcr-SCID/SCIDJcl mice (Clea Japan Inc., age at initiation of experiment: 6 weeks; hereinafter referred to as "Scid mice") were used. The mice were kept in metal mouse cages, 3 to 5 to a cage, and underwent about 1 week acclimation period prior to being subjected to the experiment. While at our facility, the animals were allowed solid feed, CRF-1 (Oriental Yeast Co., Ltd.) and tap water (from an automatic dispenser) ad libitum. Excrement was processed with an automated cleaning system. The general condition of the animals was observed upon receipt and at the completion of acclimation. Animals having no problems with general condition were used in the experiment. The animals were maintained in rooms under controlled conditions of temperature: 24±2° C., humidity: 55±15%, ventilation: 15±5 cycles/h with 100% fresh outside air, Lighting: 12-h dark/light cycles with illumination from fluorescent lights (light: 08:00 to 20:00).

3. Cancer Cell Lines and Culture Conditions

TMD8 was established from cells of a patient with diffuse large B-cell lymphoma (Tohda S et al., Leuk Res., 2006, 30: 1385-90). RPMI Medium 1640 (Invitrogen Corporation, hereinafter referred to as "RPMI") containing 10 vol % inactivated FBS and 1 vol % Penicillin-Streptomycin liquid (Invitrogen Corporation) was prepared and used as medium. The medium was stored at 5° C. (allowable range: 1° C. to 9° C.). The cell suspension of 4×106 to 2.0×107 cells per dish was inoculated in a 150 mm dish containing the medium. The plates were incubated at 37° C., 5% $CO_2$, 95% air. Cells were counted in a hemocytometer and their viability was at least 90% the day of cells injection.

4. Cell Inoculation

At Day 0, the pellet was suspended in RPMI previously cooled on ice to obtain a 2×108 cells/mL cell suspension. The RPMI cell suspension and equal volume of BD Matrigel GFR (BD Biosciences) were combined to prepare a 1×108 cells/mL cell suspension. This was used as the cell suspension for implantation. Then, 0.1 mL of cell suspension was subcutaneously injected in the right flank of the mice under pentobarbital anesthesia, using a 25-gauge needle (Terumo Corporation).

5. Treatment Schedule

When the mean tumor volume reached 100 to 200 $mm^3$ and 300 to 400 $mm^3$ mice were randomized in groups of 8-10 according to their individual tumor volumes and treatment was initiated. The mean tumor volume of each group was not different from the others (analysis of variance).

6. Observation of Condition of Xenograft-Bearing Animals

After TMD8 implantation, the general condition of all animals was recorded on each day to measure tumor volume.

7. Measurement of Tumor Diameters

The long axis and short axis of the tumors were measured with electronic calipers (Mitutoyo Corporation) every 2 or 4 days from TMD8 implantation to the final assessment day.

8. Endpoints and Assessment Methods

The primary endpoint was tumor volume on the final assessment day. In addition, the tumor growth inhibition rate (TGI, %) in the treatment groups versus the vehicle group was calculated. Temporal change in tumor volume and body weight from Day 0 were used as secondary endpoints. Tumor volume was calculated with the following formula.

Tumor volume=Long axis of tumor×(short axis of tumor)2×0.5

Individual tumor volumes were calculated to the first decimal place.

Mice were eventually be sacrificed and autopsied when tumors reach a maximum of 3,000 $mm^3$.

9. Expression and Treatment of Data 9.1. Expression of Data

Tumor volume and body weight in each group were expressed as the mean±standard error (S.E.). TGI (%) in the treated group was displayed to the first decimal place.

9.2. Statistical Analysis

Microsoft Office Excel 2007 SP-1 was used to calculate means and standard errors and to prepare tables and graphs. Statistical tests were performed with EXSUS System Ver. 7.7.1 (CAC Corporation), which is based on SAS 9.2 TS2M3 (SAS Institute Japan). Student's t test was used to compare tumor volumes in GA101 monotherapy and GA101 and compound A combination therapy. All statistical tests were two-sided, with a 5% significance level.

10. Results

Composition of Experimental Groups

TABLE 3

| Group | Drug administered dose (10 ml/kg) and route | Treatment schedule | No. of animals |
|---|---|---|---|
| Vehicle group | NaCl 0.9%/iv | Q7D × 4 | 10 |
|  | 0.5% MC/p.o. | Q0.5D × 24 |  |
| GA101 1 mg/kg group | GA101 0.1 mg/mL/iv | Q7D × 4 | 10 |
|  | 0.5% MC/p.o. | Q0.5D × 24 |  |
| GA101 3 mg/kg group | GA101 0.3 mg/mL/iv | Q7D × 4 | 10 |
|  | 0.5% MC/p.o. | Q0.5D × 24 |  |
| compound A 10 mg/kg group | NaCl 0.9%/iv | Q7D × 4 | 10 |
|  | compound A 1 mg/mL/p.o. | Q0.5D × 24 |  |
| GA101 1 mg/kg + compound A 10 mg/kg group | GA101 0.1 mg/mL/iv | Q7D × 4 | 10 |
|  | compound A 1 mg/mL/p.o. | Q0.5D × 24 |  |
| GA101 3 mg/kg + compound A 10 mg/kg group | GA101 0.3 mg/mL/iv | Q7D × 4 | 10 |
|  | compound A 1 mg/mL/p.o. | Q0.5D × 24 |  |
| Rituximab 3 mg/kg group | RTX 0.3 mg/mL/iv | Q7D × 4 | 10 |
|  | 0.5% MC/p.o. | Q0.5D × 24 |  |

FIGS. 1A-1B show that antitumor activity study of compound A in combination with GA101 in TMD8 xenograft model. At D14, when mean tumor volume was 400-450 $mm^3$, randomization of mice into 7 groups of 10 mice according to tumor volume occurred. As shown in FIGS. 1A-1B, GA101 monotherapy showed an antitumoral effect. However, the combination therapy groups appeared more active than the corresponding monotherapy. Statistical significance was observed at Days 14, 17, 21 and 24. At D35 (Day 21), 4 vehicle treated mice were sacrificed when their tumor volume was higher than 3,000 $mm^3$. All mice were sacrificed at D38 (Day 24).

In this study, the GA101-compound A combination was significantly better than the indicated monotherapy (statistical analysis shown below).

Surprisingly, we observed regression of tumor volumes at a part of individuals of D 14 and 21 in groups of 3 mg/kg of GA101 combined with 10 mg/kg of compound A, whereas no complete tumor remission was observed in the monotherapy group. These results strongly indicate that the combination therapy could be more effective against advanced tumor model.

Example 2

The experiment in Example 2 was performed according to the method described in Example 1 except for the following "substance vehicle" and "treatment schedule".

1.1. Substance Vehicle

Compound A was weighed out and suspended in a 0.5 w/v % methyl cellulose 400 cP solution (Wako Pure Chemical Industries, Ltd., hereinafter referred to as "0.5% MC"), using a mortar and pestle, to obtain a 1 mg/mL (10 mg/kg) suspension. The suspension was used within 7 days of preparation. The suspension was confirmed to be stable and uniform for 7 days under refrigeration, protected from light, and for a further 24 hours at ambient temperature exposed to indoor lighting.

The stock solutions of both GA101 (25 mg/mL) and Rituximab (10 mg/mL) were kept at 4° C. Before administration to mice, the stock solutions were diluted in NaCl 0.9% at 0.3 mg/mL (3 mg/kg) for this study.

1.2. Treatment Schedule

When the mean tumor volume reached 400 to 450 $mm^3$ mice were randomized in groups of 6 according to their individual tumor volumes and treatment was initiated. The mean tumor volume of each group was not different from the others (analysis of variance).

2. Results
Composition of Experimental Groups

TABLE 4

| Group | Drug administered dose (10 ml/kg) and route | Treatment schedule | No. of animals |
|---|---|---|---|
| Vehicle group | NaCl 0.9%/iv<br>0.5% MC/p.o. | Q7D × 4<br>Q0.5D × 24 | 10 |
| GA101<br>3 mg/kg group | GA101 0.3 mg/mL/iv<br>0.5% MC/p.o. | Q7D × 4<br>Q0.5D × 24 | 10 |
| RTX<br>3 mg/kg group | RTX 0.3 mg/mL/iv<br>0.5% MC/p.o. | Q7D × 4<br>Q0.5D × 24 | 10 |
| compound A<br>10 mg/kg group | NaCl 0.9%/iv<br>compound A 1 mg/mL/p.o. | Q7D × 4<br>Q0.5D × 24 | 10 |
| GA101 3mg/kg +<br>compound A<br>10 mg/kg group | GA101 0.3 mg/mL/iv<br>compound A 1 mg/mL/p.o. | Q7D × 4<br>Q0.5D × 24 | 10 |
| RTX 3 mg/kg +<br>compound A<br>10 mg/kg group | RTX 0.3 mg/mL/iv<br>compound A 1 mg/mL/p.o. | Q7D × 4<br>Q0.5D × 24 | 10 |

FIGS. 2A-2B show that antitumor activity study of compound A in combination with GA101/RTX in TMD8 xenograft model. At D14 (Day 0), when mean tumor volume was 400-450 mm$^3$, randomization of mice into 6 groups of 10 mice according to tumor volume occurred. As shown in FIGS. 2A-2B, each monotherapy showed an antitumoural effect. Statistical significance was observed after Day 4 for GA101 and RTX and after Day 11 for compound A. Moreover, compound A combined with GA101 or RTX at suboptimal dose of 3 mg/kg once weekly resulted in a significant inhibition of tumor growth in the TMD8 xenograft model. Statistical significance was also observed between monotherapy and compound A combination therapy, indicating that compound A combined with GA101 or RTX at a sub-optimal dose was significantly better than the respective Abs or compound A given as monotherapy. At D35 (Day 21), 3 vehicle treated mice were sacrificed when their tumor volume was higher than 3,000 mm$^3$. All mice were sacrificed at D39 (Day 25).

Tumor growth inhibition (TGI) at day 0, 4, 7, 11, 14, 18 and 21 of each group shown in below. GA101 monotherapy showed superior anti-tumor activity compared with RTX monotherapy in terms of tumor growth inhibition (TGI, 77.9% vs 54.3% at day 21).

Tumor Growth Inhibition (TGI)

TABLE 5

| Group | Days after inoculation |  |  |  |  |  |  |
|---|---|---|---|---|---|---|---|
|  | 0 | 4 | 7 | 11 | 14 | 18 | 21 |
| GA101 3 mg/kg, i.v. | 1.7 | 30.9 | 45.0 | 53.3 | 63.3 | 72.2 | 77.9 |
| RTX 3 mg/kg, i.v. | 0.7 | 25.8 | 33.2 | 36.7 | 42.4 | 42.7 | 54.3 |
| compound A 10 mg/kg | 0.0 | 13.7 | 17.6 | 34.0 | 45.8 | 46.4 | 62.6 |
| GA101 3 mg/kg, i.v. +<br>compound A 10 mg/kg | 0.5 | 27.0 | 47.4 | 62.2 | 75.6 | 84.6 | 90.2 |
| RTX 3 mg/kg, i.v. +<br>compound A 10 mg/kg | 1.4 | 25.4 | 40.1 | 55.8 | 69.3 | 78.4 | 86.4 |

Tumor diameter was measured and tumor volume was calculated every 3 or 4 days after group assignment. Tumor growth inhibition (TGI, %) in the indicated treated group, based on tumor volume in the vehicle-treated group on each measurement day, is displayed to the first decimal place.

Example 3

The experiment in Example 3 was performed according to the method described in Example 1 except for the following "substance vehicle", "route of drug administration" and "treatment schedule"

1.1 Test Substance

The comparative substance, ibrutinib (hereinafter referred to as "compound B"), was stored in sealed containers at ambient temperature, protected from light.

1.2 Route of Drug Administration

Mice were fed a commercial diet (CRF1, Oriental Yeast Co., Ltd.) supplemented with either 0.0037% (wt/wt incorporated in the pellets) of compound A or 0.012% (wt/wt incorporated in the pellets) of compound B, respectively. The dose of compound A or compound B corresponds to a daily intake of 6 or 20 mg/kg of body weight. This calculation was based on the mean daily food intakes ranged from 160 to 180 mg/g of body weight.

1.3 Treatment Schedule

Two groups (vehicle and RTX): Mice fed a normal diet (CRF1). Treatment groups: Mice fed the same diet containing compound A or compound B after randomization. Rituximab was administered intravenously at a 3 mg/kg once weekly.

2. Results
Composition of Experimental Groups

TABLE 6

| Group | Drug administered dose and route | Treatment schedule | No. of animals |
|---|---|---|---|
| Vehicle | NaCl 0.9%/iv | Q7D × 3 | 9 |
| RTX3 mg/kg | RTX 0.3 mg/mL/iv | Q7D × 3 | 9 |
| compound A | Fed a diet containing 0.0037% of compound A | Daily | 9 |
| compound B | Fed a diet containing 0.012% of compound B | Daily | 9 |
| RTX 3 mg/kg +<br>compound A | RTX 0.3 mg/mL/ivFed a diet containing 0.0037% of compound A | Q7D × 3<br>Daily | 9 |
| RTX 3 mg/kg +<br>compound B | RTX 0.3 mg/mL/iv<br>Fed a diet containing 0.012% of compound A | Q7D × 3<br>Daily | 9 |

FIG. 3 shows that antitumor activity study of compound A or compound B in combination with RTX in TMD8 xenograft model. At D14 (Day 0), when mean tumor volume was around 450 mm$^3$, randomization of mice into 6 groups of 9 mice according to tumor volume occurred. As shown in FIG. 3, each monotherapy showed an antitumoral effect. Statistical significance was observed after Day 7 for RTX and compound A and after Day 11 for compound B. No statistical significance between the each. Thus, the antitumor activity of compound A (0.0037%) is comparable to compound B (0.012%). Interestingly, compound A in combination with RTX is more effective than the respective monotherapies in the TMD8 xenograft model. Statistical significance was also observed between monotherapy and this combination therapy. Meanwhile, statistical significance was not observed between compound B in combination with RTX and respective monotherapy, indicating that compound A combined with RTX demonstrated synergistic effect.

Tumor growth inhibition (TGI) at day 0, 3, 7, 11, 14, 18 and 21 of each group shown in below. Compound A combination therapy showed superior anti-tumor activity compared with RTX monotherapy in terms of tumor growth inhibition (TGI, 91.1% vs 64.2% at day 21, p<0.001).

TABLE 7

| Group | Days after inoculation | | | | | | |
|---|---|---|---|---|---|---|---|
| | 0 | 3 | 7 | 11 | 14 | 18 | 21 |
| RTX 3 mg/kg, i.v. | 0.0 | 14.9 | 37.2 | 49.51 | 53.4 | 60.0 | 64.2 |
| compound A 0.0037% | 0.0 | 12.7 | 42.8 | 47.55 | 51.1 | 61.0 | 56.1 |
| compound B 0.012% | 0.4 | 3.2 | 19.1 | 34.91 | 40.2 | 39.2 | 47.1 |
| RTX 3 mg/kg, i.v. + compound A 0.0037% | 0.0 | 26.9 | 54.5 | 73.57 | 79.8 | 87.1 | 91.1 |
| RTX 3 mg/kg, i.v. + compound B 0.012% | 0.0 | 17.0 | 42.2 | 58.68 | 63.0 | 70.2 | 72.3 |

Tumor diameter was measured and tumor volume was calculated every 3 or 4 days after group assignment. Tumor growth inhibition (TGI, %) in the indicated treated group, based on tumor volume in the vehicle-treated group on each measurement day, is displayed to the first decimal place.

CONCLUSIONS

As a result of Example 1, Example 2 and Example 3, the combination of compound A with GA101 or RTX may be an effective treatment for ABC-DLBCL. It has been reported that compound B antagonizes RTX-dependent NK cell-mediated cytotoxicity (See, Kohrt H E et al., Blood. Vol. 123, 1957-1960, 2014). Therefore it should be noted that compound A combined with RTX or GA101 is more effective than compound B combined with RTX in this DLBCL xenograft model, indicating rationale to use these combination (compound A+RTX or GA101) in the clinical setting.

As disclosed herein and also appended in the sequence listing, the following sequences are part of the present invention:

```
                           SEQUENCES
SEQ ID NO: 1
amino acid sequence of variable region of the heavy chain (VH) of murine
monoclonal anti-CD20 antibody B-Ly1
Gly Pro Glu Leu Val Lys Pro Gly Ala Ser Val Lys Ile Ser Cys Lys
Ala Ser Gly Tyr Ala Phe Ser Tyr Ser Trp Met Asn Trp Val Lys Leu
Arg Pro Gly Gln Gly Leu Glu Trp Ile Gly Arg Ile Phe Pro Gly Asp
Gly Asp Thr Asp Tyr Asn Gly Lys Phe Lys Gly Lys Ala Thr Leu Thr
Ala Asp Lys Ser Ser Asn Thr Ala Tyr Met Gln Leu Thr Ser Leu Thr
Ser Val Asp Ser Ala Val Tyr Leu Cys Ala Arg Asn Val Phe Asp Gly
Tyr Trp Leu Val Tyr Trp Gly Gln Gly Thr Leu Val Thr Val Ser Ala SEQ ID NO: 2
amino acid sequence of variable region of the light chain (VL) of murine
monoclonal anti-CD20 antibody B-Ly1
Asn Pro Val Thr Leu Gly Thr Ser Ala Ser Ile Ser Cys Arg Ser Ser
Lys Ser Leu Leu His Ser Asn Gly Ile Thr Tyr Leu Tyr Trp Tyr Leu
Gln Lys Pro Gly Gln Ser Pro Gln Leu Leu Ile Tyr Gln Met Ser Asn
Leu Val Ser Gly Val Pro Asp Arg Phe Ser Ser Ser Gly Ser Gly Thr
Asp Phe Thr Leu Arg Ile Ser Arg Val Glu Ala Glu Asp Val Gly Val
Tyr Tyr Cys Ala Gln Asn Leu Glu Leu Pro Tyr Thr Phe Gly Gly Gly
Thr Lys Leu Glu Ile Lys Arg SEQ ID NO: 3
amino acid sequences of variable region of the heavy chain (VH) of humanized
B-Ly1 antibody (B-HH2)
Gln Val Gln Leu Val Gln Ser Gly Ala Glu Val Lys Lys Pro Gly Ser
Ser Val Lys Val Ser Cys Lys Ala Ser Gly Tyr Ala Phe Ser Tyr Ser
Trp Met Asn Trp Val Arg Gln Ala Pro Gly Gln Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser SEQ ID NO: 4
amino acid sequences of variable region of the heavy chain (VH) of humanized
B-Ly1 antibody (B-HH3)
Gln Val Gln Leu Val Gln Ser Gly Ala Glu Val Lys Lys Pro Gly Ser
Ser Val Lys Val Ser Cys Lys Ala Ser Gly Tyr Ala Phe Ser Tyr Ser
Trp Met Asn Trp Val Arg Gln Ala Pro Gly Gln Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Leu Cys
Ala Arg Asn Val Phe Asp Gly Tyr Trp Leu Val Tyr Trp Gly Gln Gly
Thr Leu Val Thr Val Ser Ser SEQ ID NO: 5
amino acid sequences of variable region of the heavy chain (VH) of humanized
B-Ly1 antibody (B-HH4)
Gln Val Gln Leu Val Gln Ser Gly Ala Glu Val Lys Lys Pro Gly Ala
Ser Val Lys Val Ser Cys Lys Ala Ser Gly Tyr Ala Phe Ser Tyr Ser
Trp Met Asn Trp Val Arg Gln Ala Pro Gly Gln Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser
```

-continued

SEQUENCES

SEQ ID NO: 6
amino acid sequences of variable region of the heavy chain (VH) of humanized
B-Ly1 antibody (B-HHS)
Gln Val Gln Leu Val Gln Ser Gly Ala Glu Val Lys Lys Pro Gly Ser
Ser Val Lys Val Ser Cys Lys Ala Ser Gly Tyr Ala Phe Ser Tyr Ser
Trp Met Ser Trp Val Arg Gln Ala Pro Gly Gln Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser SEQ ID NO: 7
amino acid sequences of variable region of the heavy chain (VH) of humanized
B-Ly1 antibody (B-HH6)
Gln Val Gln Leu Val Gln Ser Gly Ala Glu Val Lys Lys Pro Gly Ser
Ser Val Lys Val Ser Cys Lys Ala Ser Gly Tyr Ala Phe Ser Tyr Ser
Trp Ile Asn Trp Val Arg Gln Ala Pro Gly Gln Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser SEQ ID NO: 8
amino acid sequences of variable region of the heavy chain (VH) of humanized
B-Ly1 antibody (B-HH7)
Gln Val Gln Leu Val Gln Ser Gly Ala Glu Val Lys Lys Pro Gly Ser
Ser Val Lys Val Ser Cys Lys Ala Ser Gly Tyr Ala Phe Ser Tyr Ser
Trp Ile Ser Trp Val Arg Gln Ala Pro Gly Gln Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser SEQ ID NO: 9
amino acid sequences of variable region of the heavy chain (VH) of humanized
B-Ly1 antibody (B-HH8)
Gln Val Gln Leu Val Gln Ser Gly Ala Glu Val Lys Lys Pro Gly Ala
Ser Val Lys Val Ser Cys Lys Ala Ser Gly Tyr Thr Phe Thr Tyr Ser
Trp Met Asn Trp Val Arg Gln Ala Pro Gly Gln Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser SEQ ID NO: 10
amino acid sequences of variable region of the heavy chain (VH) of humanized
B-Ly1 antibody (B-HH9)
Gln Val Gln Leu Val Gln Ser Gly Ala Glu Val Lys Lys Pro Gly Ala
Ser Val Lys Val Ser Cys Lys Ala Ser Gly Tyr Thr Phe Ser Tyr Ser
Trp Met Asn Trp Val Arg Gln Ala Pro Gly Gln Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser SEQ ID NO: 11
amino acid sequences of variable region of the heavy chain (VH) of humanized
B-Ly1 antibody (B-HL8)
Glu Val Gln Leu Val Glu Ser Gly Gly Gly Leu Val Lys Pro Gly Gly
Ser Leu Arg Leu Ser Cys Ala Ala Ser Gly Phe Thr Phe Ser Tyr Ser
Trp Met Asn Trp Val Arg Gln Ala Pro Gly Lys Gly Leu Glu Trp Val
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser

| SEQUENCES |
|---|

SEQ ID NO: 12
amino acid sequences of variable region of the heavy chain (VH) of humanized
B-Ly1 antibody (B-HL10)
Glu Val Gln Leu Val Glu Ser Gly Gly Gly Leu Val Lys Pro Gly Gly
Ser Leu Arg Leu Ser Cys Ala Ala Ser Gly Phe Ala Phe Ser Tyr Ser
Trp Met Asn Trp Val Arg Gln Ala Pro Gly Lys Gly Leu Glu Trp Val
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser SEQ ID NO: 13
amino acid sequences of variable region of the heavy chain (VH) of humanized
B-Ly1 antibody (B-HL11)
Gln Val Gln Leu Val Glu Ser Gly Gly Gly Leu Val Lys Pro Gly Gly
Ser Leu Arg Leu Ser Cys Ala Ala Ser Gly Phe Thr Phe Ser Tyr Ser
Trp Met Asn Trp Val Arg Gln Ala Pro Gly Lys Gly Leu Glu Trp Val
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser SEQ ID NO: 14
amino acid sequences of variable region of the heavy chain (VH) of humanized
B-Ly1 antibody (B-HL12)
Glu Val Gln Leu Val Glu Ser Gly Ala Gly Leu Val Lys Pro Gly Gly
Ser Leu Arg Leu Ser Cys Ala Ala Ser Gly Phe Thr Phe Ser Tyr Ser
Trp Met Asn Trp Val Arg Gln Ala Pro Gly Lys Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser SEQ ID NO: 15
amino acid sequences of variable region of the heavy chain (VH) of humanized
B-Ly1 antibody (B-HL13)
Glu Val Gln Leu Val Glu Ser Gly Gly Gly Val Val Lys Pro Gly Gly
Ser Leu Arg Leu Ser Cys Ala Ala Ser Gly Phe Thr Phe Ser Tyr Ser
Trp Met Asn Trp Val Arg Gln Ala Pro Gly Lys Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser SEQ ID NO: 16
amino acid sequences of variable region of the heavy chain (VH) of humanized
B-Ly1 antibody (B-HL14)
Glu Val Gln Leu Val Glu Ser Gly Gly Gly Leu Lys Lys Pro Gly Gly
Ser Leu Arg Leu Ser Cys Ala Ala Ser Gly Phe Thr Phe Ser Tyr Ser
Trp Met Asn Trp Val Arg Gln Ala Pro Gly Lys Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser SEQ ID NO: 17
amino acid sequences of variable region of the heavy chain (VH) of humanized
B-Ly1 antibody (B-HL15)
Glu Val Gln Leu Val Glu Ser Gly Gly Gly Leu Val Lys Pro Gly Ser
Ser Leu Arg Leu Ser Cys Ala Ala Ser Gly Phe Thr Phe Ser Tyr Ser
Trp Met Asn Trp Val Arg Gln Ala Pro Gly Lys Gly Leu Glu Trp Met
Gly Arg Ile Phe Pro Gly Asp Gly Asp Thr Asp Tyr Asn Gly Lys Phe
Lys Gly Arg Val Thr Ile Thr Ala Asp Lys Ser Thr Ser Thr Ala Tyr
Met Glu Leu Ser Ser Leu Arg Ser Glu Asp Thr Ala Val Tyr Tyr Cys
Ala Arg Asn Val Phe Asp Gly Tyr Trp Leu Val Tyr Trp Gly Gln Gly
Thr Leu Val Thr Val Ser Ser

| SEQUENCES |
|---|
| SEQ ID NO: 18<br>amino acid sequences of variable region of the heavy chain (VH) of humanized<br>B-Ly1 antibody (B-HL16)<br>Glu Val Gln Leu Val Glu Ser Gly Gly Gly Leu Val Lys Pro Gly Gly<br>Ser Leu Arg Val Ser Cys Ala Ala Ser Gly Phe Thr Phe Ser Tyr Ser<br>Trp Met Asn Trp Val Arg Gln Ala Pro Gly Lys Gly Leu Glu Trp Met<br>Gly Arg Ile Phe Pro Gly Asp Gly Asp Thr Asp Tyr Asn Gly Lys Phe<br>Lys Gly Arg Val Thr Ile Thr Ala Asp Lys Ser Thr Ser Thr Ala Tyr<br>Met Glu Leu Ser Ser Leu Arg Ser Glu Asp Thr Ala Val Tyr Tyr Cys<br>Ala Arg Asn Val Phe Asp Gly Tyr Trp Leu Val Tyr Trp Gly Gln Gly<br>Thr Leu Val Thr Val Ser Ser<br><br>SEQ ID NO: 19<br>amino acid sequences of variable region of the heavy chain (VH) of humanized<br>B-Ly1 antibody (B-HL17)<br>Glu Val Gln Leu Val Glu Ser Gly Gly Gly Leu Val Lys Pro Gly Gly<br>Ser Leu Arg Leu Ser Cys Ala Ala Ser Gly Phe Thr Phe Ser Tyr Ser<br>Trp Met Asn Trp Val Arg Gln Ala Pro Gly Lys Gly Leu Glu Trp Met<br>Gly Arg Ile Phe Pro Gly Asp Gly Asp Thr Asp Tyr Asn Gly Lys Phe<br>Lys Gly Arg Val Thr Ile Thr Ala Asp Lys Ser Thr Ser Thr Ala Tyr<br>Met Glu Leu Ser Ser Leu Arg Ser Glu Asp Thr Ala Val Tyr Tyr Cys<br>Ala Arg Asn Val Phe Asp Gly Tyr Trp Leu Val Tyr Trp Gly Gln Gly<br>Thr Leu Val Thr Val Ser Ser<br><br>SEQ ID NO: 20<br>amino acid sequences of variable region of the light chain (VL) of humanized<br>B-Ly1 antibody B-KV1<br>Asp Ile Val Met Thr Gln Thr Pro Leu Ser Leu Pro Val Thr Pro Gly<br>Glu Pro Ala Ser Ile Ser Cys Arg Ser Ser Lys Ser Leu Leu His Ser<br>Asn Gly Ile Thr Tyr Leu Tyr Trp Tyr Leu Gln Lys Pro Gly Gln Ser<br>Pro Gln Leu Leu Ile Tyr Gln Met Ser Asn Leu Val Ser Gly Val Pro<br>Asp Arg Phe Ser Gly Ser Gly Ser Gly Thr Asp Phe Thr Leu Lys Ile<br>Ser Arg Val Glu Ala Glu Asp Val Gly Val Tyr Tyr Cys Ala Gln Asn<br>Leu Glu Leu Pro Tyr Thr Phe Gly Gly Gly Thr Lys Val Glu Ile Lys<br>Arg Thr Val |

---

We claim:

1. A method of treatment of a patient suffering from a B-Cell Non-Hodgkin's lymphomas or a lymphocytic leukemias, comprising the step of administering a therapeutically effective amount of rituximab in combination with a therapeutically effective amount of 6-amino-9-[(3R)-1-(2-butynoyl)-3-pyrrolidinyl]-7-(4-phenoxyphenyl)-7,9-dihydro-8H-purin-8-one or a salt thereof, to said patient in the need of such treatment.

2. The method according to claim 1, wherein said B-Cell Non-Hodgkin's lymphomas or lymphocytic leukemias is selected from the group consisting of a follicular lymphomas, Small Non-Cleaved Cell Lymphomas/Burkitt's lymphoma, marginal zone lymphomas, Mantle cell lymphoma, Large Cell Lymphoma, hairy cell leukemia, lymphocytic lymphoma, waldenstrom's macroglobulinemia, acute lymphocytic leukemia, chronic lymphocytic leukemia/small lymphocytic lymphoma, B-cell prolymphocytic leukemia, plasma cell neoplasms, plasma cell myeloma, multiple myeloma, plasmacytoma, Hodgkin's disease, post transplant lymphoproliferative disorder, HIV associated lymphoma, waldenstrom's macroglobulinemia, and primary CNS lymphoma.

3. The method according to claim 1, wherein the therapeutically effective amount of rituximab is 0.1 mg/kg to 50 mg/kg, and the therapeutically effective amount of 6-amino-9-[(3R)-1-(2-butynoyl)-3-pyrrolidinyl]-7-(4-phenoxyphenyl)-7,9-dihydro-8H-purin-8-one or a salt thereof is 1 µg/kg to 50 mg/kg.

4. The method according to claim 1, wherein the therapeutically effective amount of rituximab is 0.1 mg/kg to 20 mg/kg, and the therapeutically effective amount of 6-amino-9-[(3R)-1-(2-butynoyl)-3-pyrrolidinyl]-7-(4-phenoxyphenyl)-7,9-dihydro-8H-purin-8-one or a salt thereof is 0.1 mg/kg to 20 mg/kg.

* * * * *

SEQUENCE LISTING

<160> NUMBER OF SEQ ID NOS: 20

<210> SEQ ID NO 1
<211> LENGTH: 112
<212> TYPE: PRT
<213> ORGANISM: Mus sp.
<220> FEATURE:
<221> NAME/KEY: MISC_FEATURE
<223> OTHER INFORMATION: amino acid sequence of variable region of the
      heavy chain (VH) of murine monoclonal anti-CD20 antibody B-Ly1

<400> SEQUENCE: 1

Gly Pro Glu Leu Val Lys Pro Gly Ala Ser Val Lys Ile Ser Cys Lys
1               5                   10                  15

Ala Ser Gly Tyr Ala Phe Ser Tyr Ser Trp Met Asn Val Lys Leu
            20                  25                  30

Arg Pro Gly Gln Gly Leu Glu Trp Ile Gly Arg Ile Phe Pro Gly Asp
        35                  40                  45

Gly Asp Thr Asp Tyr Asn Gly Lys Phe Lys Gly Lys Ala Thr Leu Thr
    50                  55                  60

Ala Asp Lys Ser Ser Asn Thr Ala Tyr Met Gln Leu Thr Ser Leu Thr
65                  70                  75                  80

Ser Val Asp Ser Ala Val Tyr Leu Cys Ala Arg Asn Val Phe Asp Gly
                85                  90                  95

Tyr Trp Leu Val Tyr Trp Gly Gln Gly Thr Leu Val Thr Val Ser Ala
                100                 105                 110

```
<210> SEQ ID NO 2
<211> LENGTH: 103
<212> TYPE: PRT
<213> ORGANISM: Mus sp.
<220> FEATURE:
<221> NAME/KEY: MISC_FEATURE
<223> OTHER INFORMATION: amino acid sequence of variable region of the
      light chain (VL) of murine monoclonal anti-CD20 antibody B-Ly1

<400> SEQUENCE: 2

Asn Pro Val Thr Leu Gly Thr Ser Ala Ser Ile Ser Cys Arg Ser Ser
1               5                   10                  15

Lys Ser Leu Leu His Ser Asn Gly Ile Thr Tyr Leu Tyr Trp Tyr Leu
            20                  25                  30

Gln Lys Pro Gly Gln Ser Pro Gln Leu Leu Ile Tyr Gln Met Ser Asn
        35                  40                  45

Leu Val Ser Gly Val Pro Asp Arg Phe Ser Ser Gly Ser Gly Thr
    50                  55                  60

Asp Phe Thr Leu Arg Ile Ser Arg Val Glu Ala Glu Asp Val Gly Val
65                  70                  75                  80

Tyr Tyr Cys Ala Gln Asn Leu Glu Leu Pro Tyr Thr Phe Gly Gly Gly
                85                  90                  95

Thr Lys Leu Glu Ile Lys Arg
            100

<210> SEQ ID NO 3
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HH2)

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 4
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HH3)

<400> SEQUENCE: 4

Gln Val Gln Leu Val Gln Ser Gly Ala Glu Val Lys Lys Pro Gly Ser
```

```
                1               5                  10                  15
Ser Val Lys Val Ser Cys Lys Ala Ser Gly Tyr Ala Phe Ser Tyr Ser
                20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Leu Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 5
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HH4)

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ala Phe Ser Tyr Ser
                20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 6
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HH5)

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Met Ser Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
```

```
                    50                  55                  60
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Asn Val Phe Asp Gly Tyr Trp Leu Val Tyr Trp Gly Gln Gly
                    100                 105                 110

Thr Leu Val Thr Val Ser Ser
        115

<210> SEQ ID NO 7
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HH6)

<400> SEQUENCE: 7

Gln Val Gln Leu Val Gln Ser Gly Ala Glu Val Lys Lys Pro Gly Ser
 1                   5                  10                  15

Ser Val Lys Val Ser Cys Lys Ala Ser Gly Tyr Ala Phe Ser Tyr Ser
                    20                  25                  30

Trp Ile Asn Trp Val Arg Gln Ala Pro Gly Gln Gly Leu Glu Trp Met
                    35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Asn Val Phe Asp Gly Tyr Trp Leu Val Tyr Trp Gly Gln Gly
                    100                 105                 110

Thr Leu Val Thr Val Ser Ser
        115

<210> SEQ ID NO 8
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HH7)

<400> SEQUENCE: 8

Gln Val Gln Leu Val Gln Ser Gly Ala Glu Val Lys Lys Pro Gly Ser
 1                   5                  10                  15

Ser Val Lys Val Ser Cys Lys Ala Ser Gly Tyr Ala Phe Ser Tyr Ser
                    20                  25                  30

Trp Ile Ser Trp Val Arg Gln Ala Pro Gly Gln Gly Leu Glu Trp Met
                    35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Asn Val Phe Asp Gly Tyr Trp Leu Val Tyr Trp Gly Gln Gly
```

-continued

```
                      100                 105                 110

Thr Leu Val Thr Val Ser Ser
        115

<210> SEQ ID NO 9
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HH8)

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 10
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HH9)

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 11
<211> LENGTH: 119
<212> TYPE: PRT
```

```
<213> ORGANISM: Artificial
<220> FEATURE:
<223> OTHER INFORMATION: amino acid sequences of variable region of the
      heavy chain (VH) of humanized B-Ly1 antibody (B-HL8)

<400> SEQUENCE: 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 12
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HL10)

<400> SEQUENCE: 12

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 13
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HL11)

<400> SEQUENCE: 13

Gln Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
            115

<210> SEQ ID NO 14
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HL12)

<400> SEQUENCE: 14

Glu Val Gln Leu Val Glu Ser Gly Ala Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
            115

<210> SEQ ID NO 15
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HL13)

<400> SEQUENCE: 15

Glu Val Gln Leu Val Glu Ser Gly Gly Gly Val Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
50                  55                  60
```

```
Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 16
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HL14)

<400> SEQUENCE: 16

Glu Val Gln Leu Val Glu Ser Gly Gly Gly Leu Lys Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 17
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HL15)

<400> SEQUENCE: 17

Glu Val Gln Leu Val Glu Ser Gly Gly Gly Leu Val Lys Pro Gly Ser
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110
```

Thr Leu Val Thr Val Ser Ser
        115

<210> SEQ ID NO 18
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HL16)

<400> SEQUENCE: 18

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 19
<211> LENGTH: 119
<212> TYPE: PRT
<213> ORGANISM: Artificial
<220> FEATURE:
<223> OTHER INFORMATION: amino acid sequences of variable region of the
      heavy chain (VH) of humanized B-Ly1 antibody (B-HL17)

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 20
<211> LENGTH: 115
<212> TYPE: PRT
<213> ORGANISM: Artificial

-continued

```
<220> FEATURE:
<223> OTHER INFORMATION: amino acid sequences of variable region of the
      light chain (VL) of humanized B-Ly1 antibody B-KV1

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val
        115
```